(12) United States Patent
Bikson et al.

(10) Patent No.: US 10,143,832 B2
(45) Date of Patent: Dec. 4, 2018

(54) ELECTRODE ASSEMBLIES FOR DELIVERING THERAPEUTIC ELECTROSTIMULATION

(71) Applicant: Research Foundation of the City University of New York, New York, NY (US)

(72) Inventors: Marom Bikson, Brooklyn, NY (US); Abhishek Datta, New York, NY (US); Niranjan Khadka, Jackson Heights, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 170 days.

(21) Appl. No.: 14/936,038

(22) Filed: Nov. 9, 2015

(65) Prior Publication Data
US 2016/0129237 A1  May 12, 2016

Related U.S. Application Data

(60) Provisional application No. 62/076,833, filed on Nov. 7, 2014.

(51) Int. Cl.
*A61N 1/04* (2006.01)
*A61N 1/36* (2006.01)

(52) U.S. Cl.
CPC ......... *A61N 1/0456* (2013.01); *A61N 1/0476* (2013.01); *A61N 1/0492* (2013.01); *A61N 1/36025* (2013.01); *A61N 1/048* (2013.01)

(58) Field of Classification Search
CPC ............. A61N 1/0456; A61N 1/36025; A61N 1/0492; A61N 1/0476; A61N 1/048
See application file for complete search history.

(56) References Cited

U.S. PATENT DOCUMENTS

| | | | |
|---|---|---|---|
| 5,487,759 A * | 1/1996 | Bastyr | A61N 1/36021 607/115 |
| 8,494,627 B2 | 7/2013 | Bikson et al. | |
| 8,718,778 B2 | 5/2014 | Bikson et al. | |
| 8,818,515 B2 | 8/2014 | Bikson et al. | |
| 8,965,514 B2 | 2/2015 | Bikson et al. | |
| 2010/0137779 A1* | 6/2010 | Seitz | A61N 1/30 604/20 |
| 2015/0343196 A1* | 12/2015 | Vasapollo | A61N 1/048 607/45 |

* cited by examiner

*Primary Examiner* — Rex R Holmes
(74) *Attorney, Agent, or Firm* — Hoffmann & Baron, LLP

(57) ABSTRACT

An apparatus for delivering therapeutic electrostimulation across a tissue surface includes a current source, a low current component adapted to contact the tissue surface, a first electrode assembly electrically connected to the current source and supported by the low current component, a second electrode assembly electrically connected to the current source and supported by the low current component and a conductive fluid supported by the low current component for facilitating a flow of electric current across the tissue surface. At least one of the first and second electrodes assemblies includes at least one of a magnetic electrode, a high current component and a non-current component.

13 Claims, 37 Drawing Sheets

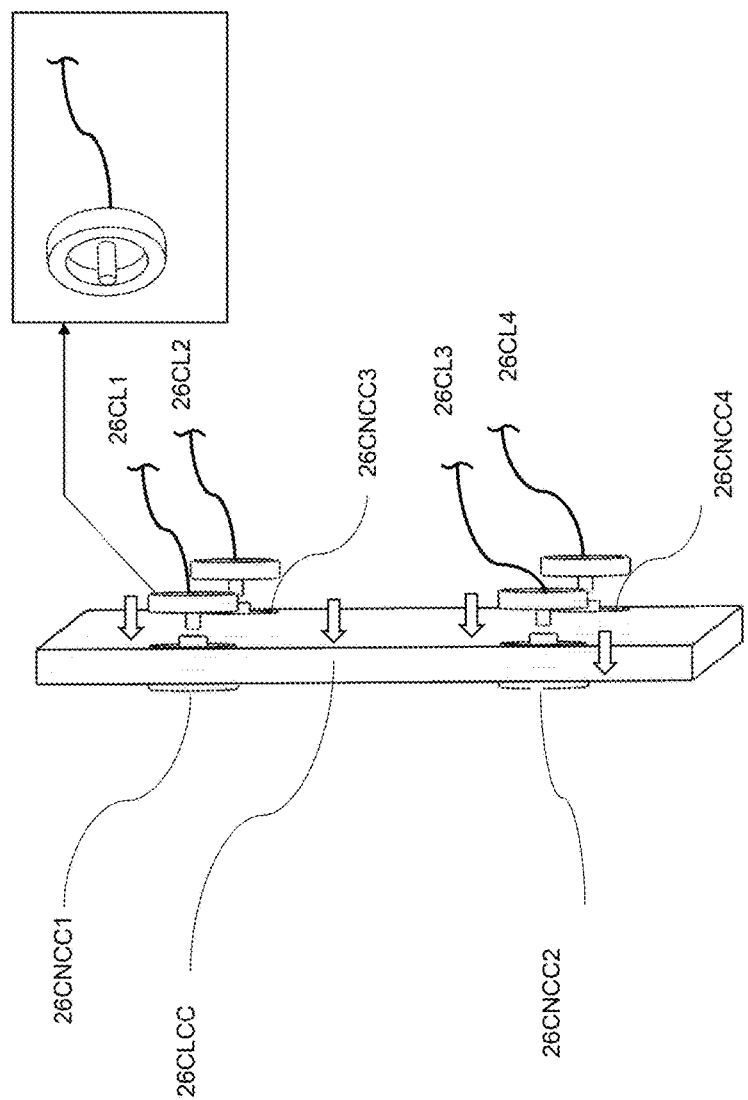

ELECTRODE ASSEMBLIES FOR DELIVERING THERAPEUTIC ELECTROSTIMULATION

CROSS-REFERENCE TO RELATED APPLICATION

This application claims the benefit of U.S. Provisional Application No. 62/076,833, filed on Nov. 7, 2014, which is incorporated herein by reference in its entirety for all purposes.

BACKGROUND

This specification generally relates to apparatus for electrostimulation of body tissue, including methods of transcranial electrostimulation. For example, plastic changes in brain function can be safely induced in humans by low-intensity electrical stimulation through scalp electrodes. Such electrical stimulation is known as transcranial electrostimulation (TES). These changes can be potentially used for therapeutic or performance enhancing applications.

Transcranial direct current stimulation (TDCS) is a non-invasive neurotechnology, which applies small constant currents (ranging from 0.2 to 2 mA) to the surface of the scalp to achieve neural modulation. TDCS has shown promise in treatment for neurological disorders such as epilepsy, depression, Alzheimer's disease, Parkinson's disease, pain and stroke. It has also been shown to improve cognitive functions, such as memory and learning in healthy individuals. There has also been a recent increase in research on alternating current stimulation (TACS) to affect cognitive function.

Conventional methods for delivering transcranial electric stimulation generally involve the placing of simple individual sponge-type electrode pads on the head of the patient. Accordingly, there is a need in the art for improved electrode assemblies, which provide enhanced stability and accurate placement of electrodes.

SUMMARY

This specification describes systems and methods relating to electrostimulation of body tissue including methods relating to electrostimulation of transcranial tissue.

In general, one innovative aspect of the subject matter described in this specification can be embodied in an apparatus for delivering therapeutic electrostimulation across a tissue surface, wherein the apparatus includes a current source, a low current component adapted to contact the tissue surface, a first electrode assembly electrically connected to the current source and supported by the low current component, a second electrode assembly electrically connected to the current source and supported by the low current component and a conductive fluid supported by the low current component for facilitating a flow of electric current across the tissue surface. At least one of the first and second electrodes assemblies includes at least one of a magnetic electrode, a high current component and a non-current component.

In a preferred aspect, the low current component includes a generally planar upper layer and a generally planar lower layer disposed substantially parallel with the upper layer. The lower layer is adapted to contact the tissue surface and the conductive fluid is disposed between the upper layer and the lower layer. In this embodiment, at least one of the first and second electrode assemblies extends through the upper layer of the low current component and contacts the conductive fluid. Preferably, this electrode assembly extending through the upper layer does not contact the lower layer of the low current component.

In another aspect, at least one of the first and second electrode assemblies includes a high current component fixed in the low current component and a magnetic electrode releasably coupled to the high current component. In another aspect, the apparatus further includes a current multiplexor electronically connected between the current source and the first and second electrode assemblies.

BRIEF DESCRIPTION OF THE DRAWINGS

FIG. 26C depicts a side view of another possible example of an electrode assembly with current leads, non-current members, and low current component.

DETAILED DESCRIPTION

Figure 1:
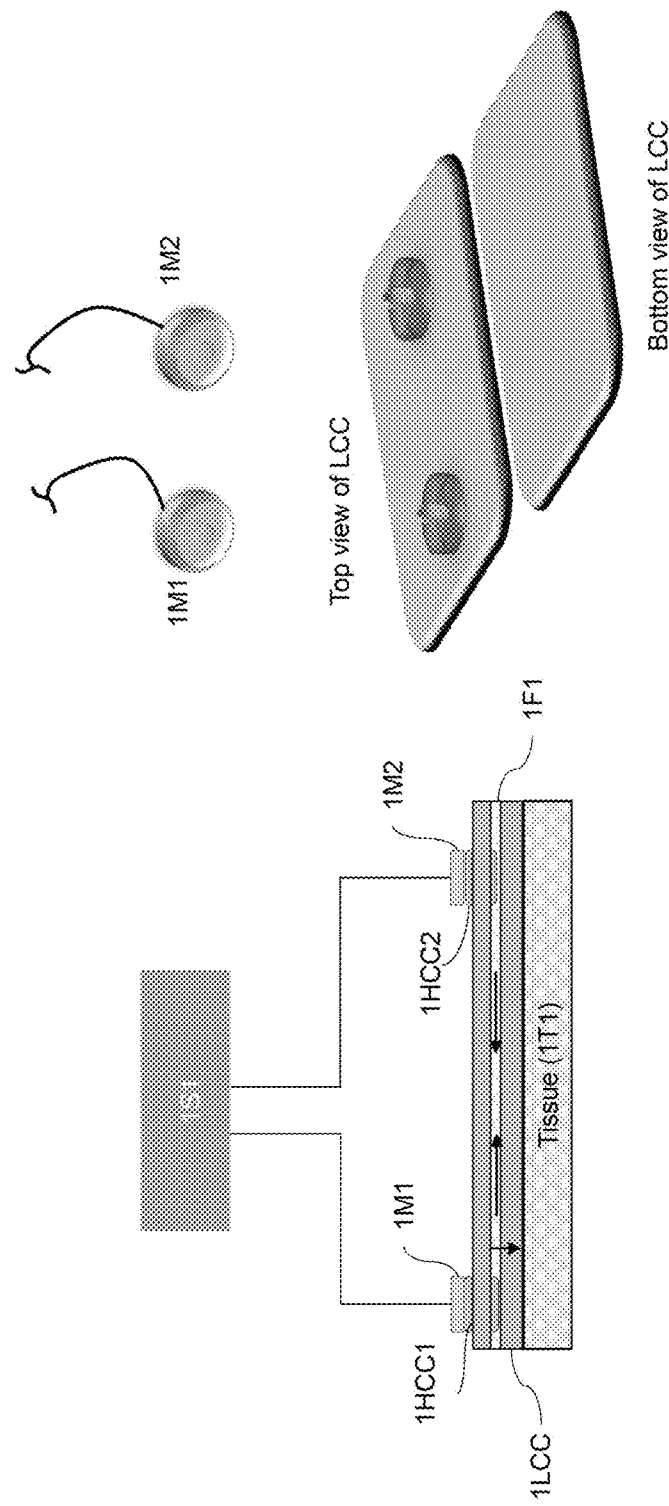
FIG. 1 is a cross-section view of an electro-magnetic apparatus on top of a tissue with magnetic electrodes, high current components, and low current component.

FIG. 1 illustrates an embodiment of a rigid connection in between magnetic electrodes 1M1 and 1M2 and high current components 1HCC1 and 1HCC2 to ensure mechanical stability and efficacy of the apparatus and during electrical stimulation. The magnetic electrodes 1M1 and 1M2 have magnetic properties, while the high current components 1HCC1 and 1HCC2 are made from a ferro-magnetic material to permit a releasable magnetic coupling between the two. The high current components 1HCC1 and 1HCC2 are supported in a low current component 1LCC1 made from a material that blocks high current values, but allows a flow of low current therethrough. The low current component 1LCC1 is generally planar or pad-like and is adapted to be applied to a tissue surface 1T1.

In one embodiment, the high current components 1HCC1 and 1HCC2 are fixed within apertures formed in the low current component 1LCC and protrude through the low current component 1LCC1 so as to permit magnetic coupling between the magnetic electrodes 1M1 and 1M2 and the high current components 1HCC1 and 1HCC2 on one side of the low current component 1LCC1, while a portion of each high current component 1HCC1 and 1HCC2 is exposed on the opposite side of the low current compo9nent 1LCC1.

In one embodiment, the low current component 1LCC1 has two layers with the high current components 1HCC1 and 1HCC2 provided in a top layer and a bottom layer is adapted to make contact with the tissue surface 1T1. In this embodiment, there is a porous pocket of conductive fluid 1F1 provided between the layers of the low current component. The lower layer of the low current component may also be presoaked with the conductive fluid to ensure maximum current flow from the system to the skin and increase electrochemical performance.

The magnetic electrodes 1M1 and 1M2 are both connected to individual ports of a current source 1S1. The magnetic electrodes 1M1 and 1M2 are further magnetically and electrically connected to the high current components 1HCC1 and 1HCC2, but not directly connected to the low current component 1LCC. The high current components 1HCC1 and 1HCC2 are connected to the magnetic electrodes and the top layer of the low current component 1LCC and are also in electrical contact with the conductive fluid F1, but are not in direct electrical contact with the bottom layer of the low current component 1LCC.

The magnetic electrodes 1M1 and 1M2 can be provided with structure that cooperates with structure provided on the high current components 1HCC1 and 1HCC2 to provide a more rigid and stable connection therebetween. For example, the magnetic electrodes can be provided with a protrusion and the high current components can be provided with a recess that receives the protrusion in a snap-fit engagement. Thus, the male snap of the magnetic electrodes and the female snap of the high current components make a rigid connection.

The number of magnetic electrodes is equal to the number of high current components and is one more than the number of current sources. In general, the magnetic electrodes 1M1 and 1M2 are in contact with 1HCC1 and 1HCC2 and also in contact with the low current component 1LCC, but not completely. Embedded parts of the high current components 1HCC1 and 1HCC2 are surrounded by the conductive fluid 1F1 and are in between the top and bottom section of 1LCC. The bottom layer of the low current component 1LCC is in contact with the tissue.

Figure 2:
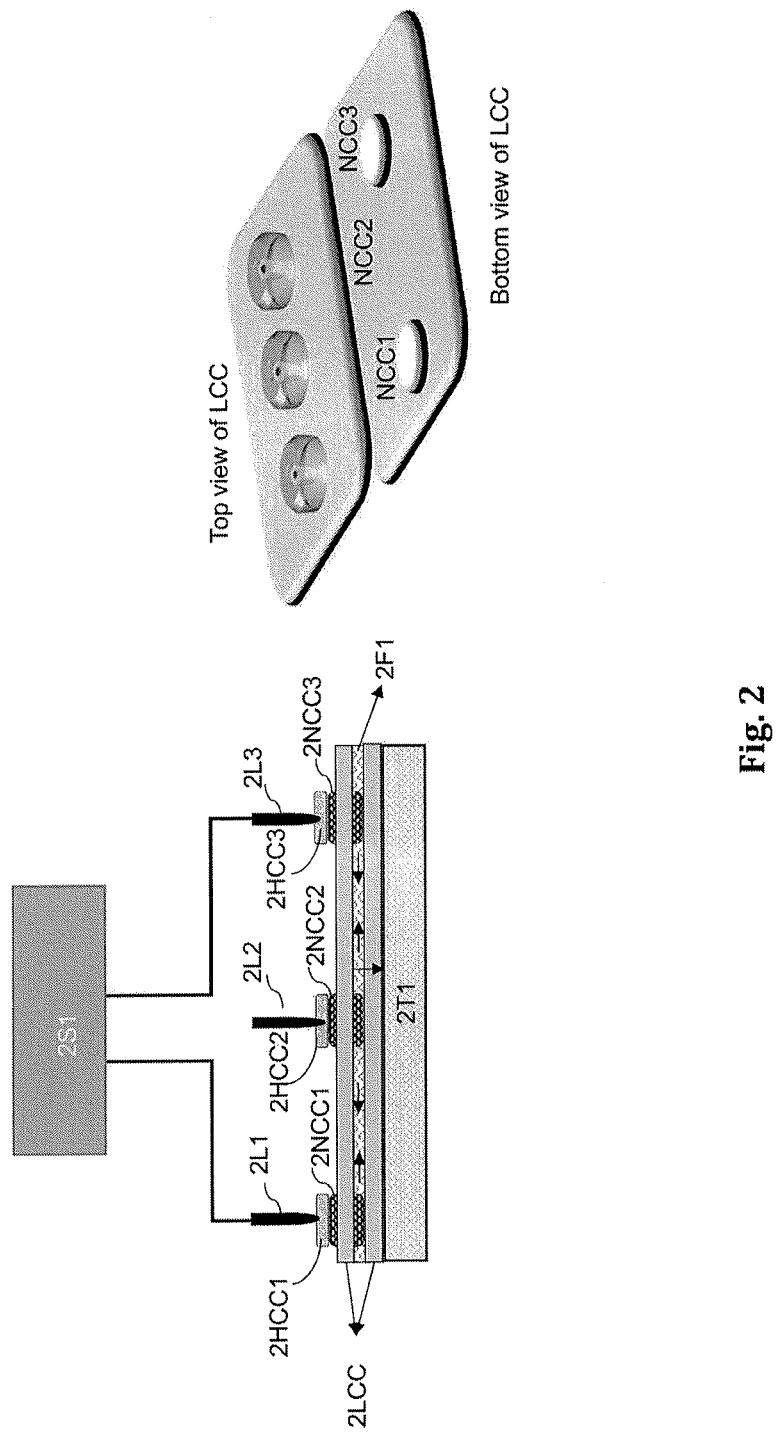
FIG. 2 is a cross-section and perspective views of an electrode assembly of high current components, non-current members, and low current component with a porous pocket of conductive fluid.

FIG. 2 shows another embodiment where there is a rigid connection between high current components 2HCC1, 2HCC2 and 2HCC3 and non-current members 2NCC1, 2NCC2 and 2NCC3 for effectively delivering current around the non-current members and hence maximizing the robustness of the apparatus. Such rigid connection can be provided via snap structure, as described above.

In this embodiment, three high current components are provide, wherein two of the high current components 2HCC1 and 2HCC3 are connected to a current source 2S1, while one high current component 2HCC2 is not. Electric leads 2L1, 2L2, and 2L3 are in contact with respective high current components 2HCC1, 2HCC2, and 2HCC3. The high current components 2HCC1, 2HCC2, and 2HCC3 are rigidly connected to the non-current components 2NCC1, 2NCC2, and 2NCC3 and the non-current components are embedded into and protrude through a top layer of a low current component 2LCC to make contact with a lower layer of the low current component. Again, the bottom layer of the low current component 2LCC is in contact with the tissue surface 2T1 and the gap between the upper and lower layers of the low current component 2LCC is filled with conductive fluid 2F1. Generally, the number of nonconductive members in contact with the bottom layer of the low current component is equal to the number of electric leads connected to the high current components and is two more than the number of low current components and current sources.

Figure 3:
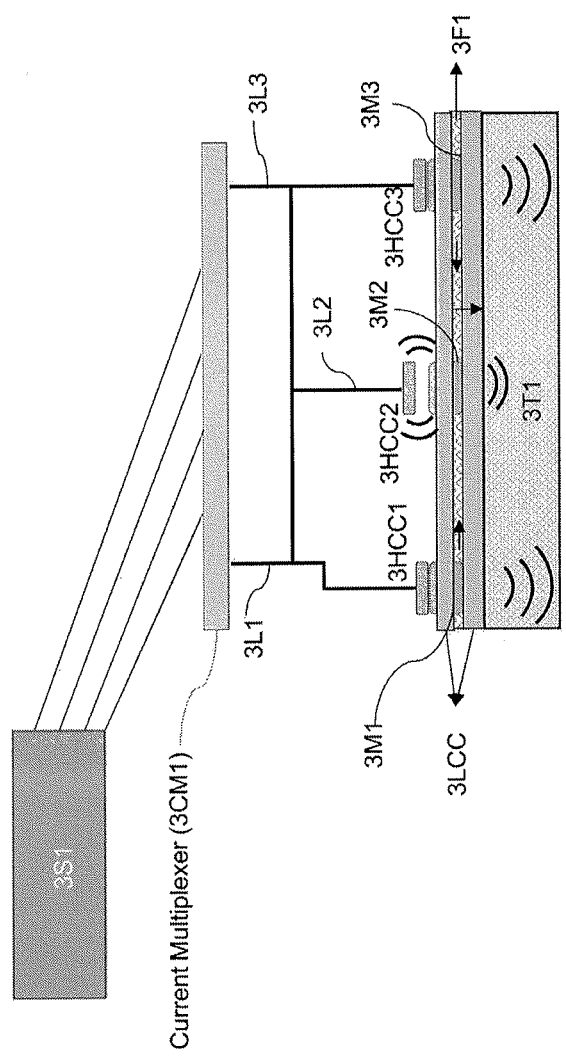
FIG. 3 is another example of a cross section view of an electro-magnetic apparatus with independent high current components, shared high current component, magnetic electrode, and low current component.

FIG. 3 depicts another embodiment where a resultant field effect of both high current components 3HCC1, 3HCC2 and 3HCC3 and magnetic electrodes 3M1, 3M2 and 3M3 is seen when there is a rigid connection between them. In contrast, shared current leads and the high current component's proximity tend to generate less combined field compared to the rigidly connected ones. This system ensures maximum electrochemical stability. Three leads 3L1, 3L2, and 3L3 are all connected to a current source 3S 1 through a current multiplexer 3CM. A shared second lead 3L2 is connected to both a first lead 3L1 and a third lead 3L3. The shared second lead 3L2 is connected to a second high current component 3HCC2, but is not connected to a second magnetic electrode 3M2. The first and third high current components 3HCC1 and 3HCC3 are rigidly connected with respective first and third magnetic electrodes 3M1 and 3M3. However, the second high current component 3HCC2 is not in contact with the second magnetic electrode 3M2. The rigid connection between the first high current component 3HCC1 and the first magnetic electrode 3M1, and between the third high current component 3HCC3 and the third magnetic electrode 3M3 allows more current injection inside the tissue, as compared to the proximity connection between the second magnetic electrode 3M2 and the second high current component 3HCC2, where there is no direct contact therebetween.

The three magnetic electrodes 3M1, 3M2, and 3M3 are all embedded inside an upper layer of a low current component 3LCC and are surrounded by a conductive fluid 3F1. A lower layer of the low current component 3LCC is in contact with the tissue 3T1. Generally, the number of high current components not connected to a respective magnetic electrode is equal to one less than the number of high current components connected to a respective magnetic electrode and is one less than the number of wire leads coming out of the current multiplexer.

Figure 4:
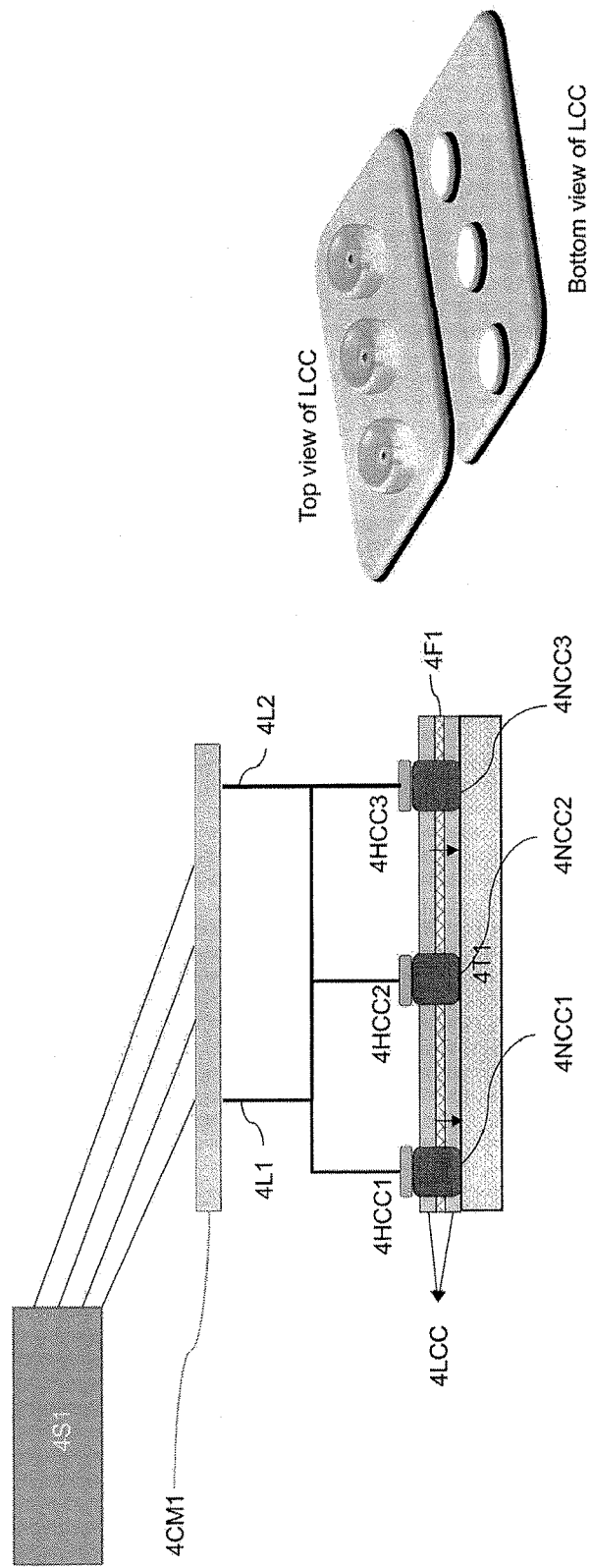
FIG. 4 is another example of a cross section and perspective views of an electrode assembly with a shared high current component, independent high current components, non-current members and low current component with a porous pocket of conductive fluid.

FIG. 4 illustrates another embodiment where the non-current members are rigidly connected to the high current components and are in contact with the tissue to deliver even current around the non-current members. In this embodiment, a second high current component 4HCC2 is connected to two leads 4L1 and 4L2 from a current multiplexor 4CM1. Each high current component 4HCC1, 4HCC2, and 4HCC3 is connected to a respective non-current component 4NCC1, 4NCC2, 4NCC3, and each non-current component is in embedded within and extends through a lower layer of a low current member 4LCC. The lower layer of the low current component 4LCC is in contact with the tissue surface 4T1 and the gap between the upper and lower layers of the low current component 4LCC is filled with a conductive fluid 4F1 that surrounds the embedded parts of all non-current members. In general, the number of high current components shared in the entire assembly is two less than the total number of high current components rigidly connected to the non-current member and is also equal to 1 less than the number of leads coming out of the current multiplexer. This assembly is preferable for safety and tolerability during electrical stimulation.

Figure 5:
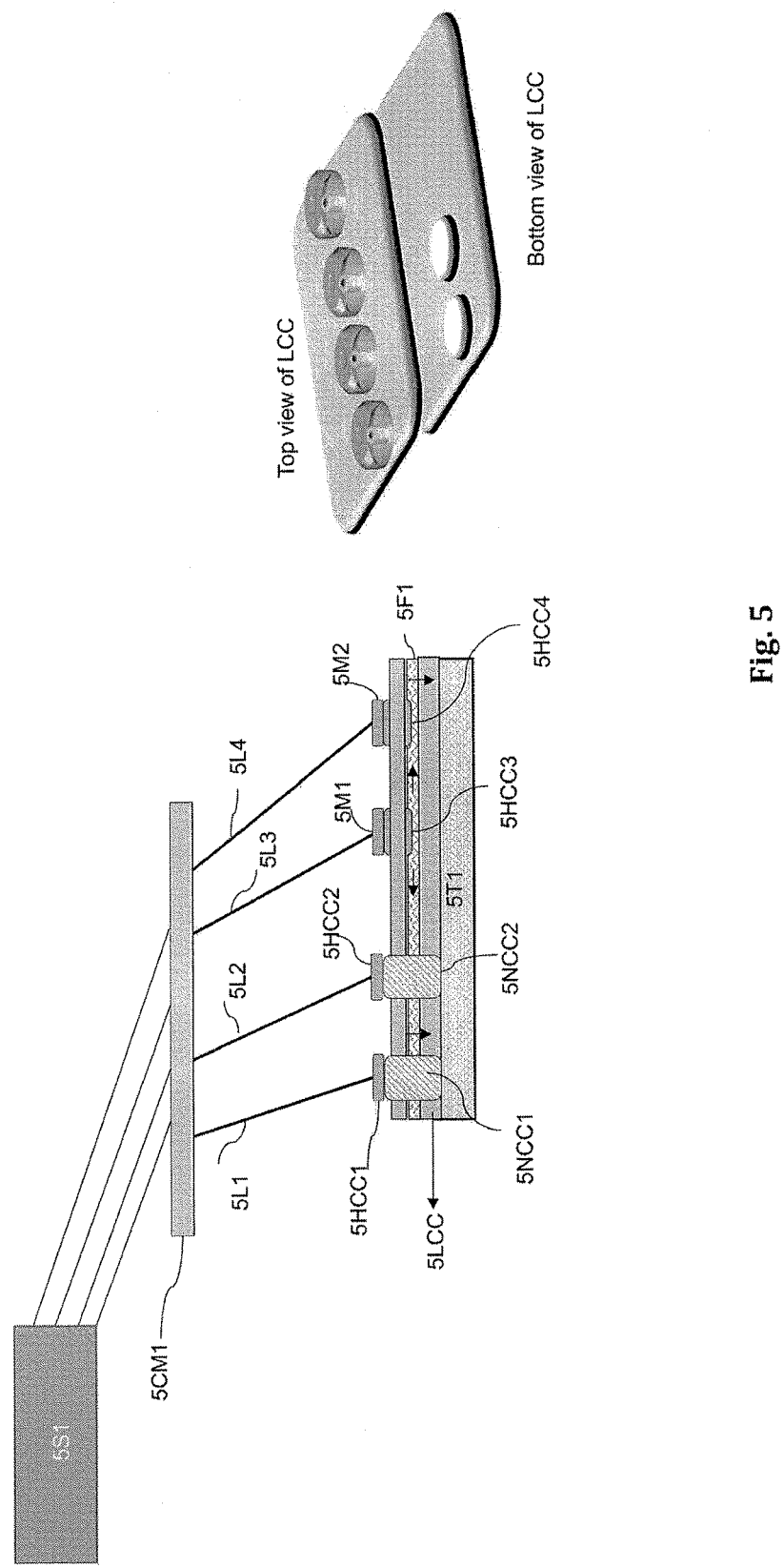
FIG. 5 is another possible example of a cross-section and perspective views of an electro-magnetic apparatus with magnetic electrodes, high current components, non-current components, and low current component.

FIG. 5 depicts another embodiment where two high current components are suspended in the conductive fluid, whereas the non-current members are in contact with the tissue. Both of these high current components 5HCC1 and 5HCC2 are connected to respective non-current components 5NCC1 and 5NCC2 and are also connected to a bottom layer of a low current component 5LCC. Two magnetic electrodes 5M1 and 5M2 are connected rigidly to other high current components 5HCC3 and 5HCC4, but are not in contact with the lower layer of the low current component 5LCC. The embedded parts of the non-current components 5NCC1, 5NCC2 and the two other high current components 5HCC3, and 5HCC4 are surrounded by a conductive fluid 5F1, which is provided between the upper and lower layers of the low current component 5LCC. In the same embodiment, 5HCC1, 5HCC2, 5M1, and 5M2 are connected through electric leads 5L1, 5L2, 5L3 and 5L4 to a multiplexor 5CM1 which is further connected to a neuro-electrical stimulation device (for e.g., tDCS device) 5S1.

Generally, the number of magnetic electrodes connected to high current components is equal to the number of high current components connected to non-current members. Moreover, the number of electrodes not in contact with the lower layer of the low current component is equal to the number of leads coming out of the multiplexor 5CM1. One advantage of this assembly is that if there is an uneven current density distribution in the low current component (for e.g. due to any poor contact between the components or lack of enough conductive fluid in the low current component), current steering produced within the magnetic electrode and other high current component (in contact) can compensate the current distribution.

Figure 6:
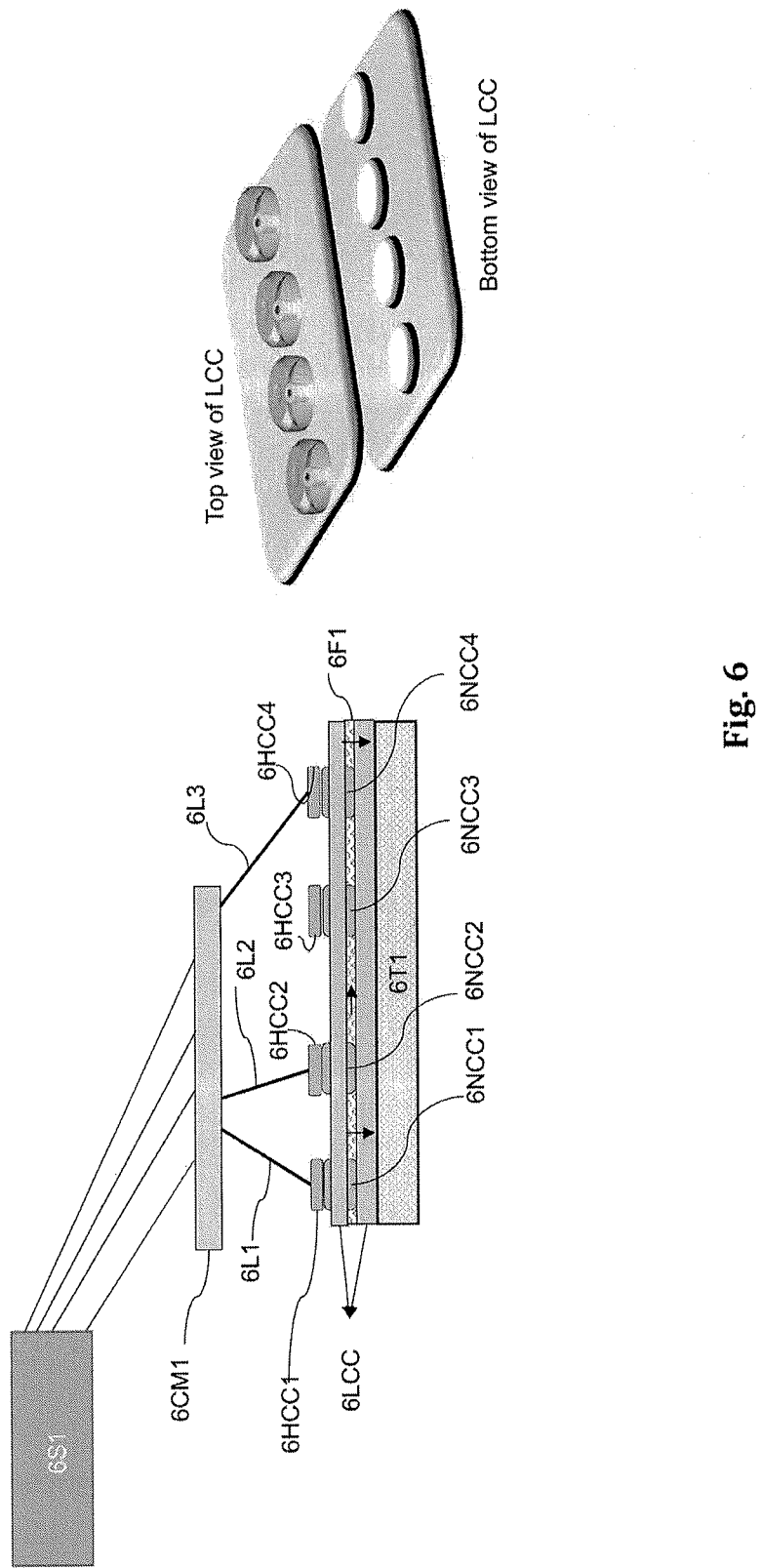
FIG. 6 is another possible example of a cross-section and perspective views of electrode assembly with a high current component, non-current members, and low current component.

FIG. 6 illustrates another embodiment when there is poor contact in between a high current component and a non-current component and also a rigidly connected high current component and non-current component, which is not connected to a current source. Three high current components 6HCC1, 6HCC2, and 6HCC4 are connected to respective leads 6L1, 6L2 and 6L4, leaving one high current component 6HCC3 not connected to a lead. All of the high current components 6HCC1, 6HCC2, 6HCC3, and 6HCC4 are rigidly connected to respective non-current components 6NCC1, 6NCC2, 6NCC3, and 6NCC4 and parts of these non-current members are embedded within a low current component 6LCC and are surrounded by a conductive fluid 6F1. A lower layer of the low current component 6LCC is in contact with the tissue surface 6T1.

In general, the number of high current components not connected to the current multiplexer 6CM1 is equal to the number of electrodes connected to the non-current components minus three. Having any number of high current components rigidly connected to the non-current component not only helps evenly distribute current density over the low current component but also ensure proper tissue/electrode interface.

Figure 7:
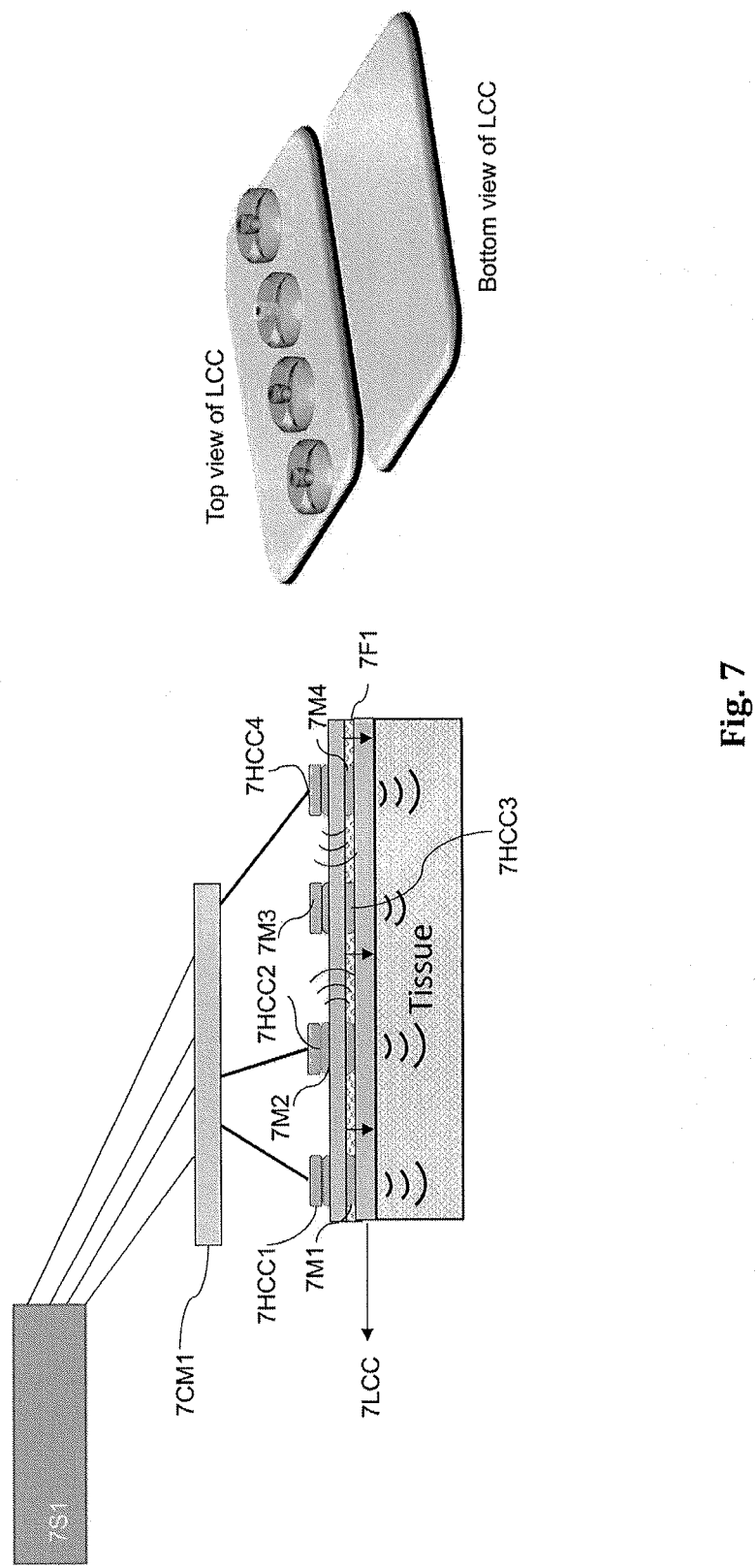
FIG. 7 is another possible example of cross-section and perspective views of electro-magnetic stimulation apparatus with magnetic electrodes and high current components.

FIG. 7 shows another embodiment where there is a rigid connection between high current components and magnetic electrodes. Three high current components 7HCC1, 7HCC2, 7HCC4 are all connected to a current source 7S1 through a current multiplexor 7CM leaving one high current component 7HCC3 with a respective magnetic electrode 7M3 not connected to the current source. Three magnetic electrodes 7M1, 7M2 and 7M4 are respectively in contact with the three high current components 7HCC1, 7HCC2 and 7HCC4 and their embedded parts are surrounded by a conductive fluid 7F1 provided between an upper and a lower layer of a low current component.

Generally, the number of magnetic electrodes rigidly connected to high current components and not connected to the current source is equal to the number of high current components connected to the magnetic electrode minus two. Moreover, the number of high current components connected to the current source is equal to the number of high current component connected to the magnetic electrode plus two. This system is preferable in a sense that the combined electro-magnetic field will bring about more uniform current distribution in the low current member and eventually to the tissue. In addition, any high current component in contact with a magnetic electrode can also be benefited (can produce electrochemical effect on the tissue) by the neighboring current steering produced within the electrodes.

Figure 8:
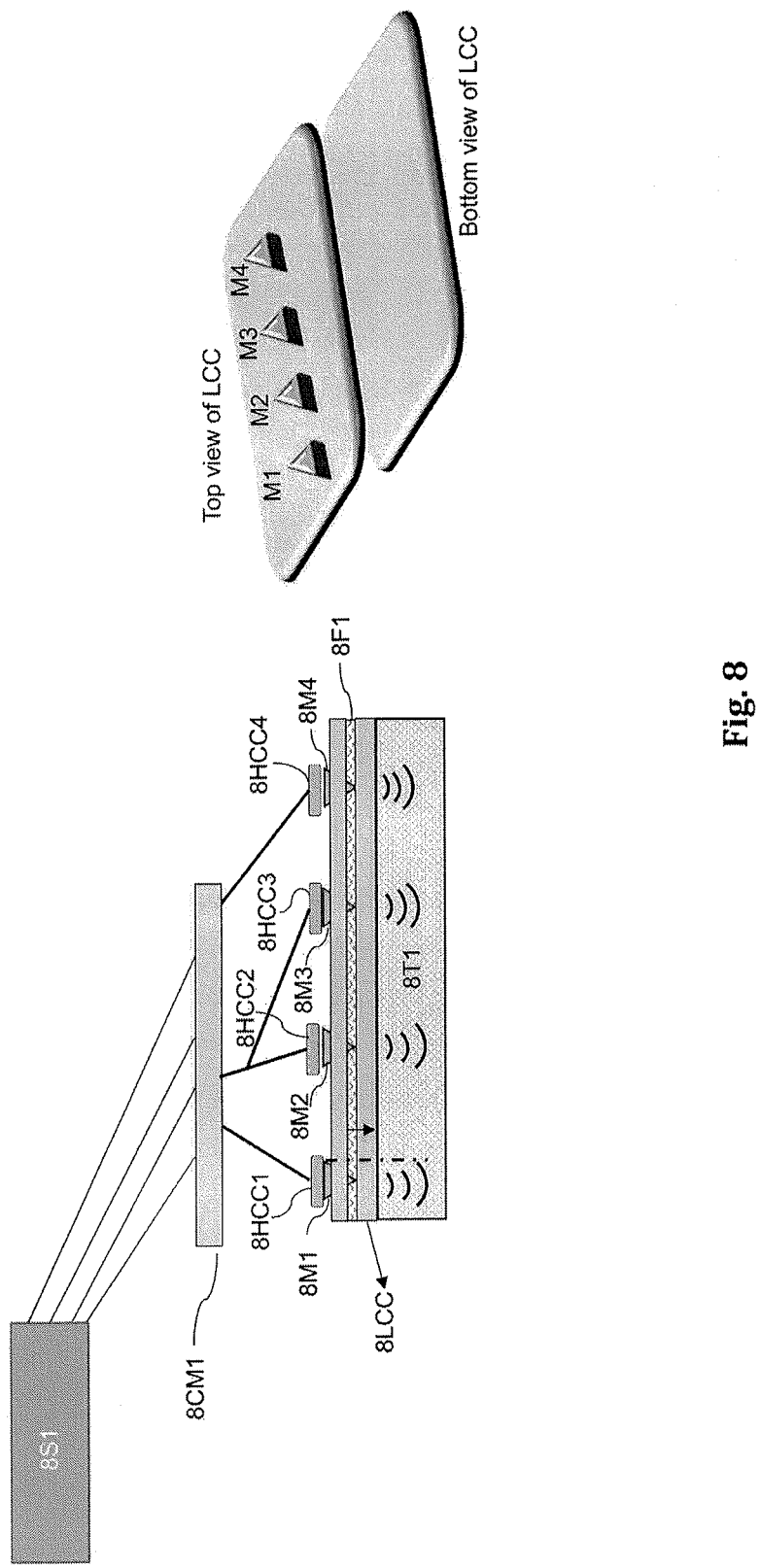
FIG. 8 is another possible example of cross-section and perspective views of electro-magnetic stimulation apparatus with high current components, magnetic electrodes, and low current component.

FIG. 8 depicts another embodiment where two high current components share the same current source. In another embodiment, one of the high current sources sharing the same port has poor contact with the corresponding magnetic electrode. In addition, there is a poor contact between another active high current component and its corresponding magnetic electrode. High current components 8HCC2 and 8HCC3 share the same lead, whereas two other high current components 8HCC1 and 8HCC4 share different and independent leads. These two other high current components 8HCC1 and 8HCC3 are connected to magnetic electrodes 8M1 and 8M3, but the two high current components 8HCC2 and 8HCC4 are not connected to magnetic electrodes 8M2 and 8M4 respectively. The embedded parts of all of the magnetic electrodes 8M1, 8M2, 8M3, and 8M4 are in contact with the lower layer of a low current component 8LCC and are surrounded by a conductive fluid 8F1.

In general, the number of high current components not connected to magnetic electrodes is equal to the number of magnetic electrodes in contact with high current components. This electro-magnetic apparatus ensures uniform and even current density distribution throughout the low current component by means of within electrode current steering even though there are poor contacts between some components of the apparatus.

Figure 9:
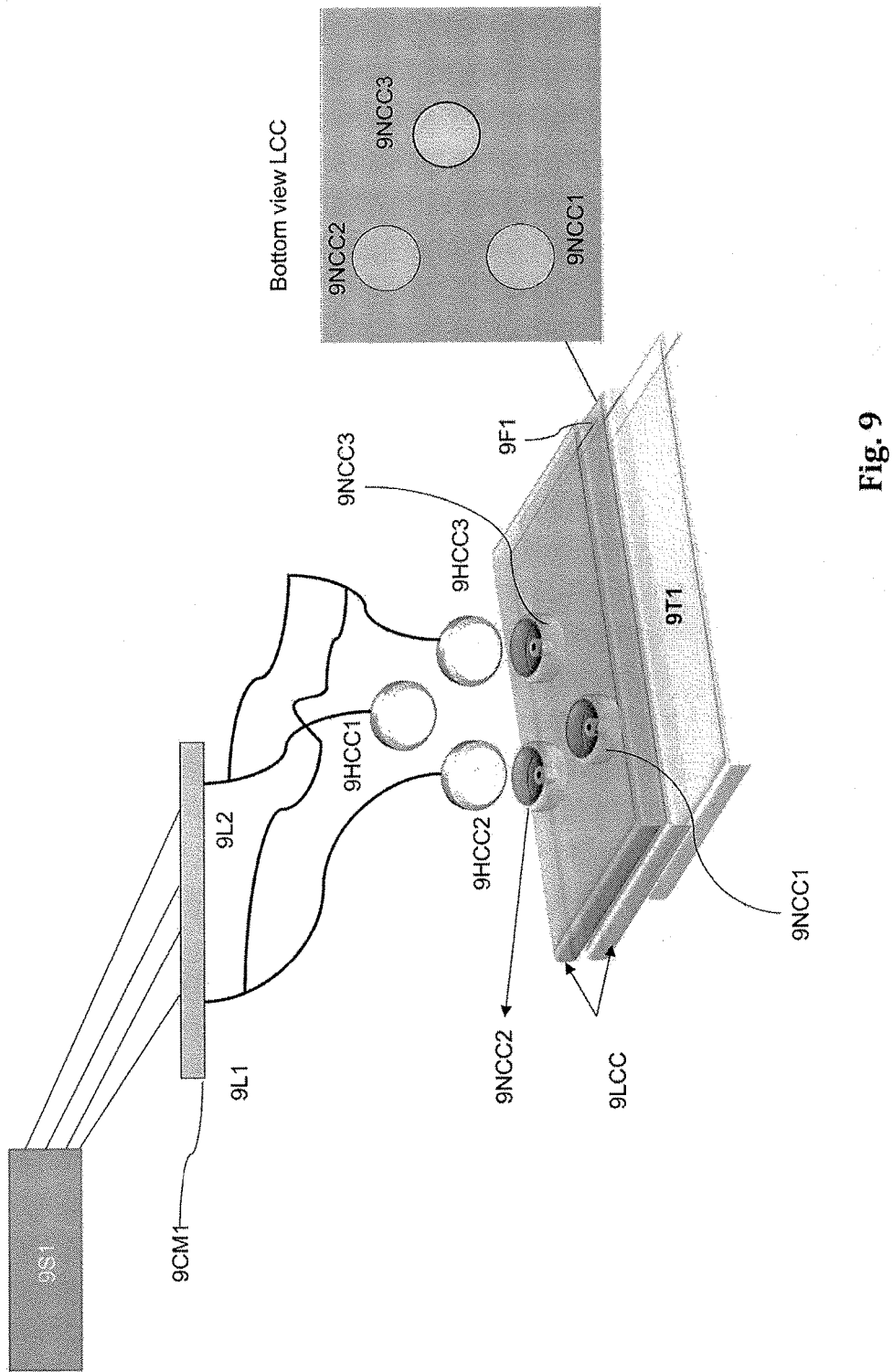
FIG. 9 is another possible example of perspective views of an electrode assembly with high current components, non-current members, and low current component.

FIG. 9 is an illustration of another embodiment where one high current component shares two current sources. The one high current component 9HCC3 shares two leads 9L1 and 9L2, but two other high current components 9HCC2, 9HCC1 do not share the same lead. Male/female snap structure of each high current component 9HCC1, 9HCC2, and 9HCC3 may be connected to cooperating female/male snap structure of non-current components 9NCC1, 9NCC2, and 9NCC3 completely or partially. The low current component 9LCC here is provided in three layers and may be presoaked with a conductive fluid 9F1, or have porous pockets filled with conductive fluid. The non-current components 9NCC1, 9NCC2, and 9NCC3 may be totally or partially immersed into the conductive fluid 9F1 and may also extend up to a middle layer of the low current component, or they may extend all the way through the bottom layer, but not to the tissue surface 9T1. Instead, the lower layer of the low current component 9LCC is in contact with the tissue surface 9T1.

In this embodiment, the number of high current component sharing both leads of the current source is equal to the total number of high current component minus two. This system is preferable in a sense that if either of the high current components connected to the respective independent current leads malfunctioned (have poor contact) the shared high current component will compensate the resultant current density distribution throughout the low current component.

Figure 10:
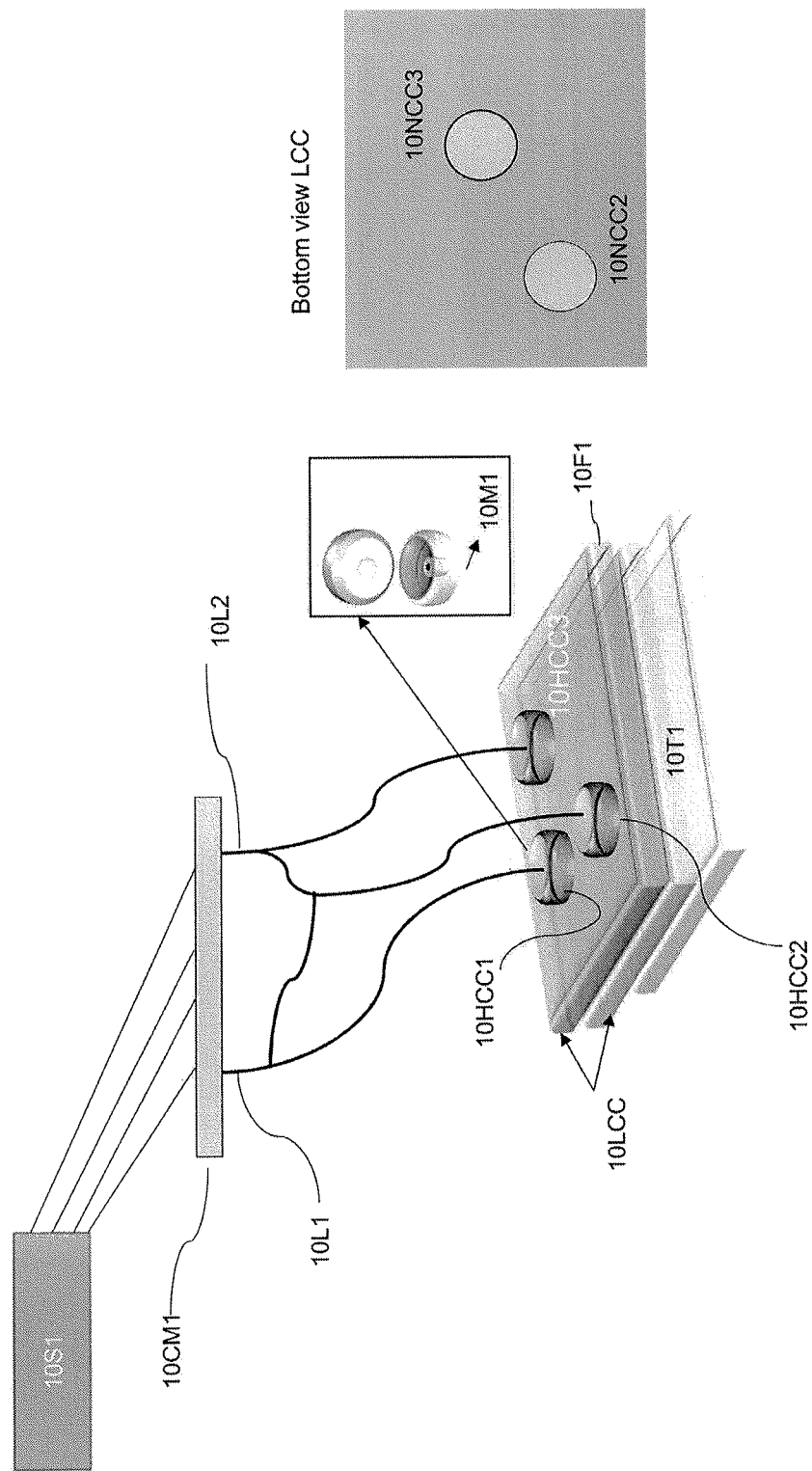
FIG. 10 is another possible example of perspective views of electrode assembly in an electro-magnetic apparatus with high current components, magnetic electrode, non-current members, and low current component.

FIG. 10 shows another embodiment similar to FIG. 9, but magnetic electrodes are used in place of the non-current members. Specifically, a high current component 10HCC2 is connected to two leads 10L1 and 10L2, whereas two other high current components 10HCC1 and 10HCC3 are connected to independent leads from a current multiplexor 10CM1. One high current component having a single lead 10HCC1 is connected to a magnetic electrode 10M1, the one high current component having two leads 10HCC2 is connected to a non-current component 10NCC2, and the other high current component having a single lead connected to 10HCC3 is connected to another non-current component respectively. The magnetic electrode 10M1, and the non-current components 10NCC2, and 10NCC3 may be suspended or fully immersed in a conductive fluid 10F1 or presoaked lower layer of a low current component 10LCC. The lower layer of the low current member 10LCC is in contact with the tissue surface 10T1.

In this embodiment, the total number of electrodes touching the lower layer of the low current component is equal to the number of high current components connected to the independent leads from the current source plus one. Moreover, the total number of magnetic electrodes firmly connected to the high current component is one less than the total number of high current components connected with the non-current members. As one independent high current component connected to the magnetic electrode turns faulty or lack proper contact, the shared high current component in rigid contact with the respective magnetic electrode will generate uniform combined electro-magnetic field and hence even current density distribution over low current component.

Figure 11:
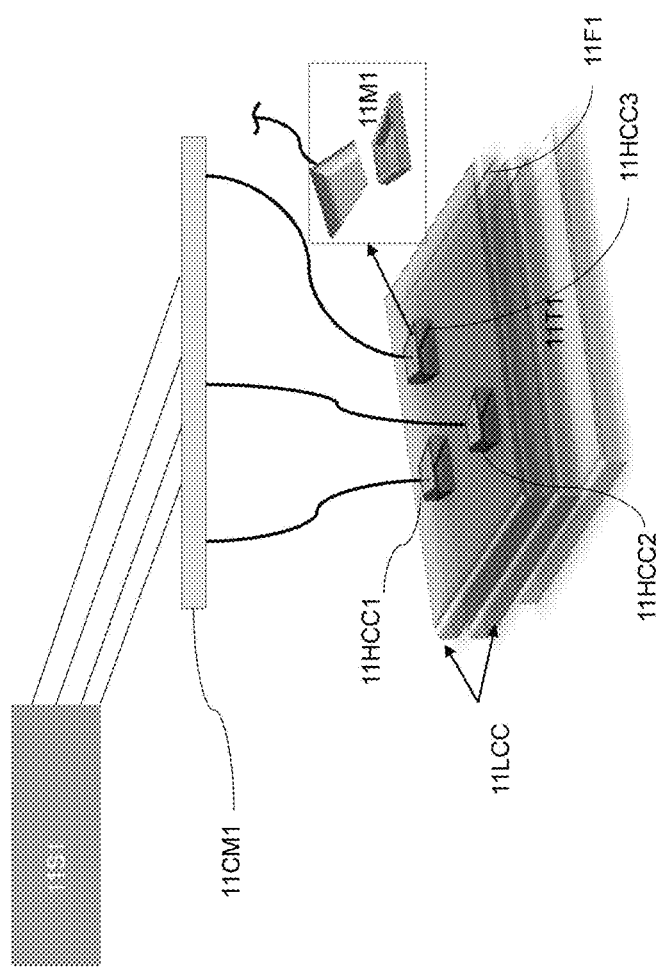
FIG. 11 is another example of a possible side view of an electro-magnetic apparatus with high current component, magnetic electrodes, and low current component.

FIG. 11 is another illustration of an embodiment similar to those of FIGS. 9 and 10, wherein high current components of different shape and their respective magnetic electrodes are used in the electrode assembly. High current components 11HCC1, 11HCC2, and 11HCC3 do not share same leads coming from a current multiplexor 11CM1. Also, these high current components 11HCC1, 11HCC2, and 11HCC3 may be rigidly or loosely in contact with respective magnetic electrodes 11M1, 11M2, and 11M3, which are suspended partially or fully in a conductive fluid 11F1 or in a pocket filled with the conductive fluid. The conductive fluid 11F1 may be present in a lower section of the top layer of a low current component 11LCC, or in the middle section between the layers, or in the upper portion of the lower layer. The lower layer of the low current component 11LCC is in contact with the tissue surface 11T1.

In this embodiment, the number of high current components connected with the magnetic electrodes either partially or fully suspended in the conductive fluid is equal to the number of leads coming out from the current multiplexor 11CM1. This system provides maximum mechanical stability, consistency, and convenience of the electrode assembly for brain stimulation.

Figure 12:
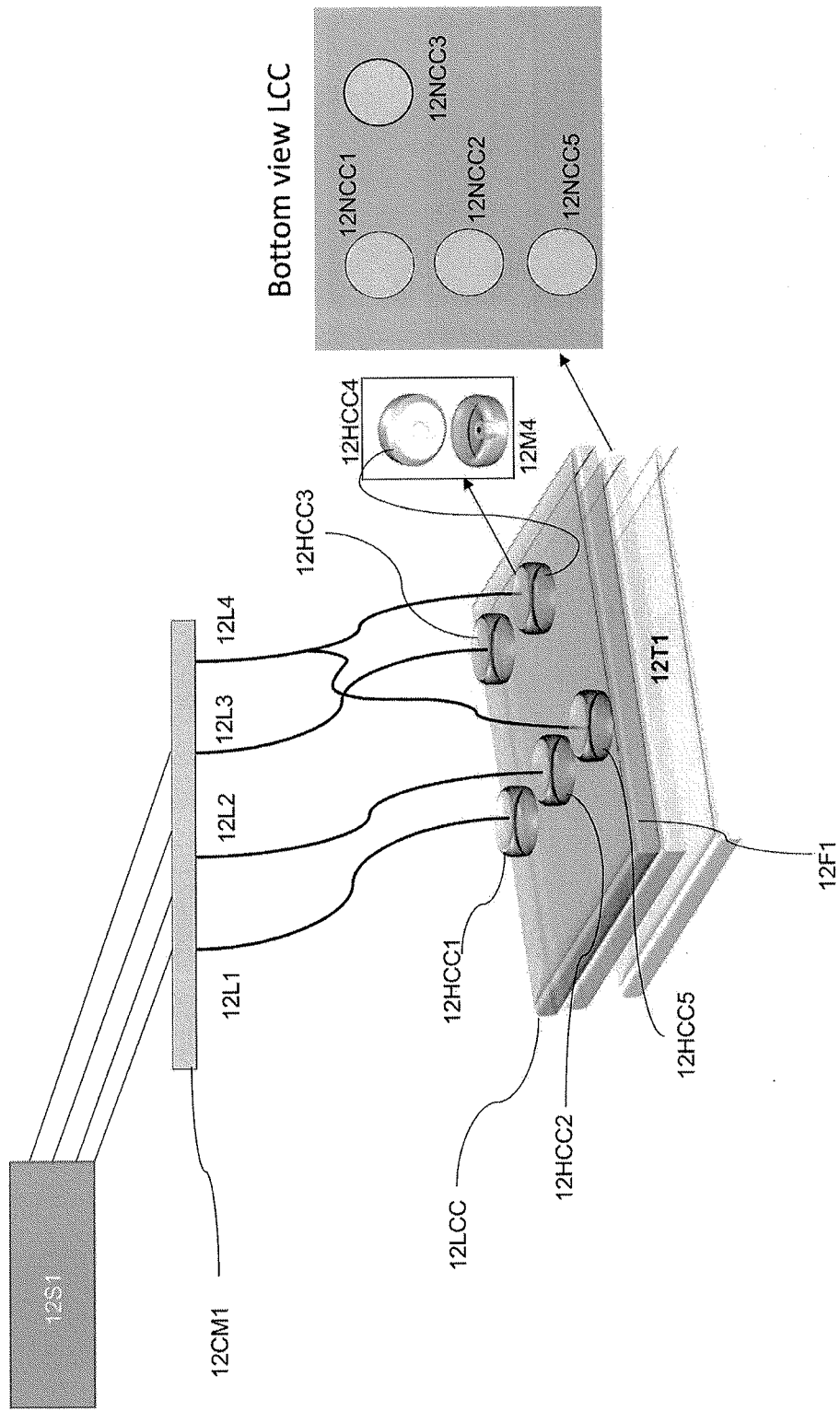
FIG. 12 is another example of possible perspective views of electrode assembly in an electro-magnetic neuromodulation apparatus with high current components, magnetic electrodes, non-current members, and low current component.

FIG. 12 is an illustration of another embodiment wherein there are multiple high current components and a shared current lead. In addition, unlike other high current components, one of the shared components is connected to a magnetic electrode. Thus, two high current components 12HCC4 and 12HCC5 are connected to one lead 12L4, whereas three other high current components 12HCC1, 12HCC2, and 12HCC3 are connected to independent leads 12L1, 12L2, and 12L3. The three high current components 12HCC1, 12HCC2 and 12HCC3 connected to independent leads are rigidly connected to respective non-current components 12NCC1, 12NCC2 and 12NCC3, while one of the high current components 12HCC5 sharing a lead is connected to its own non-current component 12NCC5. These non-current components are surrounded by a conductive fluid 12F1 and are extended throughout the thickness of the low current component 12LCC. The remaining high current component 12HCC4 on the other hand is rigidly in contact with a magnetic electrode 12M4 and is suspended partially in the conductive fluid 12F1.

In this embodiment, the number of high current components connected to non-current members is equal to the number of high current components connected to the magnetic electrodes plus three. This type of electrode assembly electrochemical stability, electrochemical performance and hence aid in neuromodulation.

Figure 13:
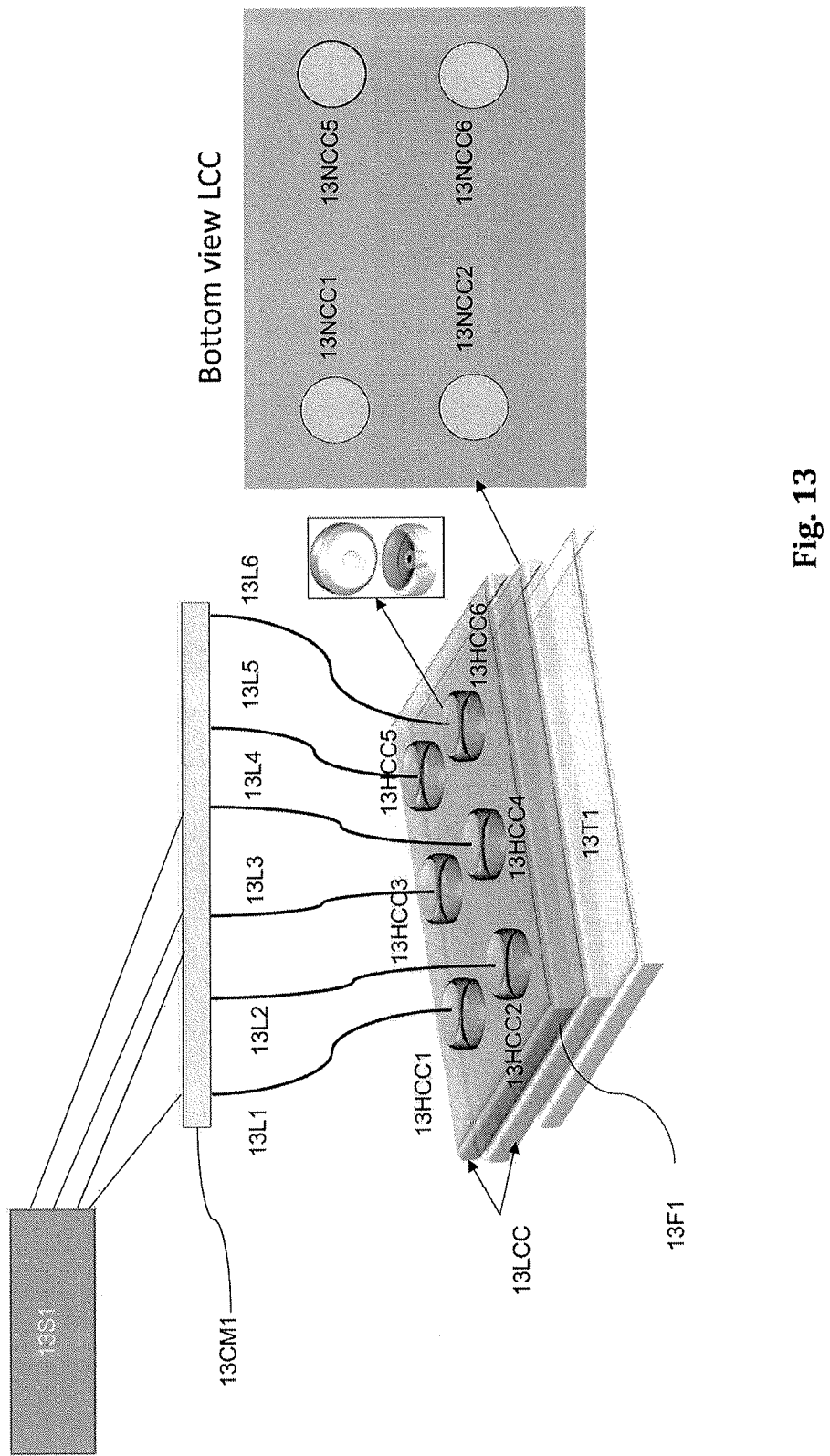
FIG. 13 is another example of possible perspective views of electrode assembly with high current components, non-current members, and low current components.

FIG. 13 is a variation of the embodiment shown in FIG. 12, but with fewer current leads connected to the high current components compared to the non-current members. Here, high current components 13HCC1, 13HCC2, 13HCC3, 13HCC4, 13HCC5, and 13HCC6 do not share a common lead from the current multiplexor 13CM1. Four of the high current components 13HCC1, 13HCC2, 13HCC5 and 13HCC6 are respectively rigidly connected to non-current components 13NCC1, 13NCC2, 13NCC5, and 13NCC6 that are extended all the way to the base of a low current component 13LCC and are surrounded by a pocket of conductive fluid 13F1 that is found in the lower section of a top layer of the low current component 13LCC or in an upper section of a bottom layer of the low current component 13LCC. Two high current components 13HCC3 and 13HCC4 are connected to their respective leads and are suspended somewhere in the middle of the pocket filled with conductive fluid 13F1.

In this embodiment, the number of high current components in contact with the low current components and are suspended partially in the pocket filled with conductive fluid is equal to the number of high current components rigidly connected to non-current components minus two. Similar to the assembly in FIG. 12, this embodiment also ensures consistency in electrochemical performance and robustness of the entire system.

Figure 14:
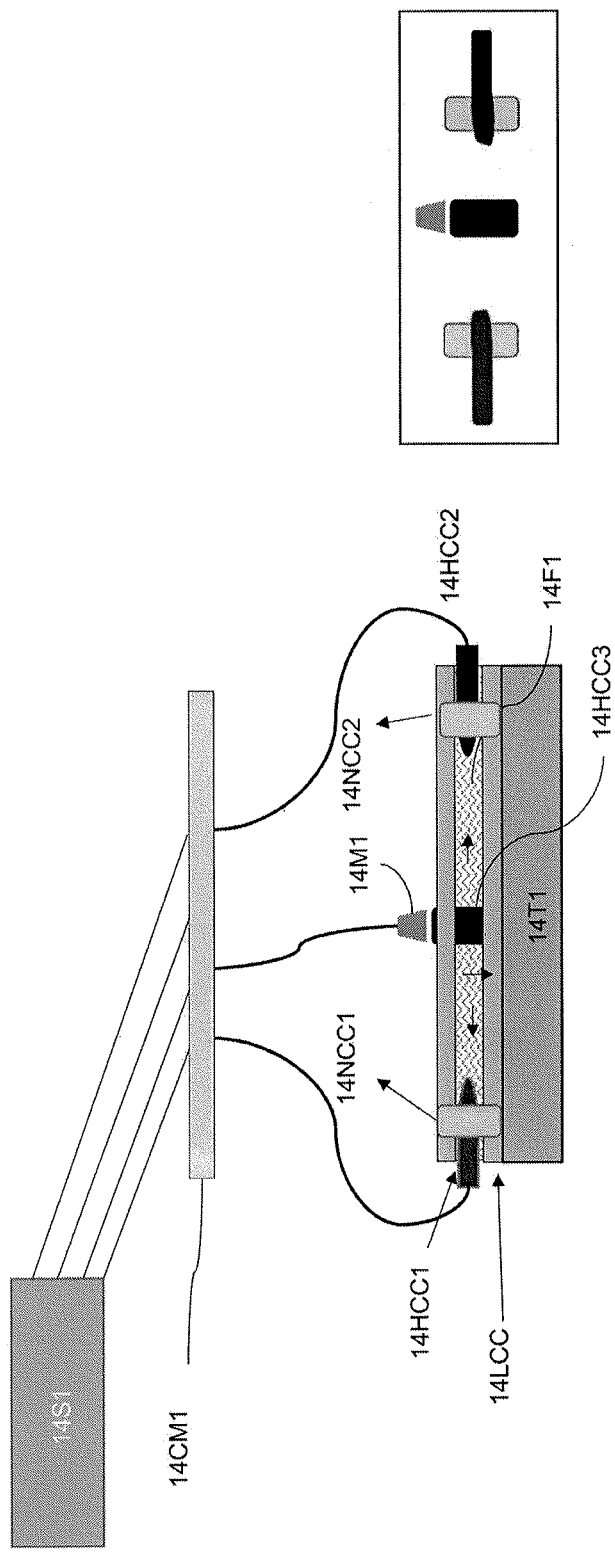
FIG. 14 is another example of possible cross-section views of electro-magnetic apparatus with magnetic electrode, high current components, and low current component.

FIG. 14 depicts another embodiment where high current components are in contact with the non-current members from lateral ends of the low current member. In addition there is not a rigid contact in between magnetic electrode and a high current component. Here, a magnetic electrode 14M1 is placed proximal to a high current component 14HCC3, whereas two other high current components 14HCC1 and 14HCC2 are in contact with respective low current components 14NCC1 and 14NCC2. The three high current components 14HCC1, 14HCC2, and 14HCC3 are in contact with the lower layer of the low current component 14LCC and this section is further in contact with the tissue. A conductive fluid 14F1 is filled in a pocket between the lower layers of top section of the low current component 14LCC and is extended to the base of the low current component 14LCC making a contact in between the tissue and the conductive fluid.

In this embodiment, the number of high current components in contact with the conductive fluid is equal to the number of magnetic electrodes plus two. Moreover, the number of non-current members in contact with the high current components is equal to one less than the total number of high current component. This assembly confirms consistency and efficacy of the system during transcranial brain stimulation.

Figure 15:
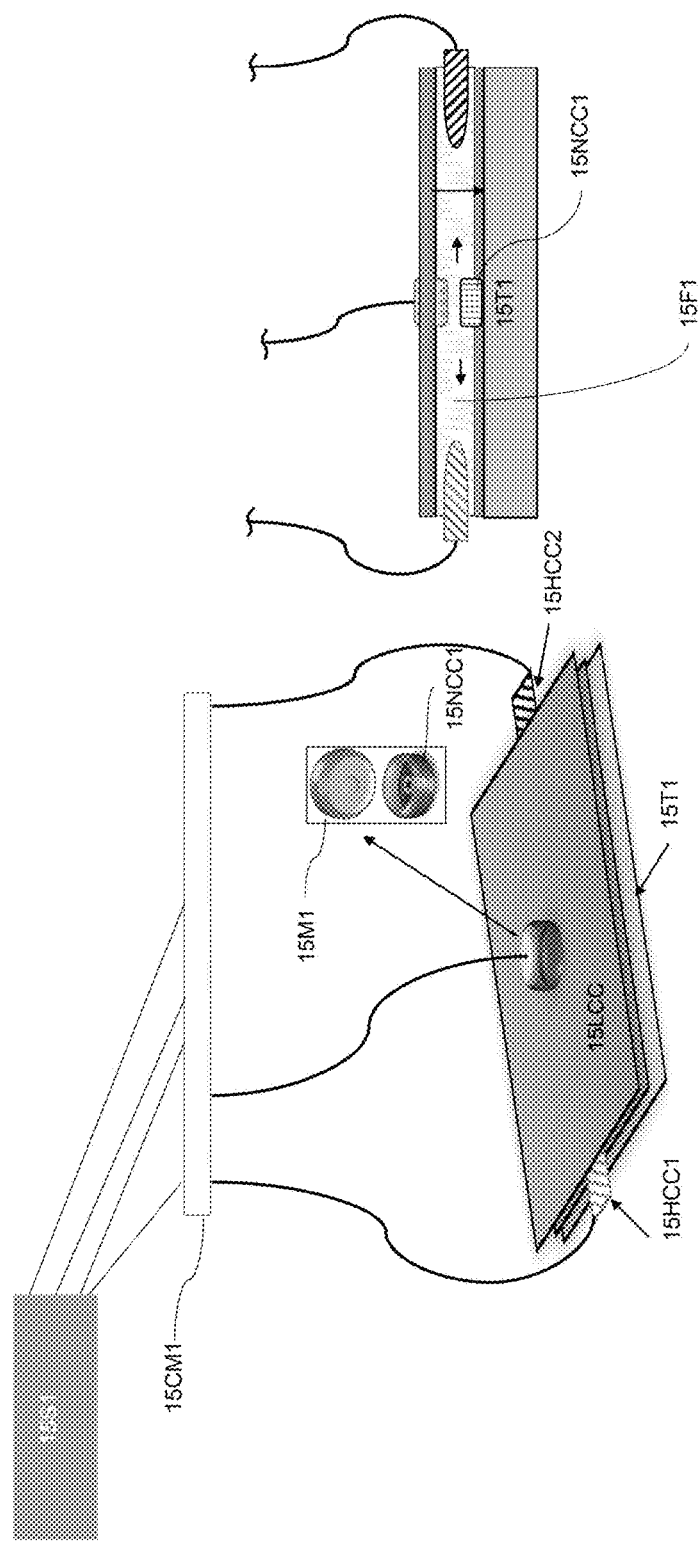
FIG. 15 is another possible example of perspective and cross-section view of electrode assembly with high current components, magnetic electrode, non-current member, and low current component.

FIG. 15 is an illustration of another embodiment similar to that shown in FIG. 14 with the magnetic electrode suspended inside the conductive fluid close to a non-current component. Two high current components 15HCC1 and 15HCC2 are totally in contact with the conductive fluid 15F1, whereas a magnetic electrode 15M1 is partially submerged in the pocket filled with conductive fluid 15F1. Also, a non-current component 15NCC1 is proximal to the magnetic electrode. The lower layer of the low current component 15LCC is in contact with the tissue in such a way that the pocket filled with conductive fluid 15F1 and the non-current component 15NCC1 touches the tissue.

In this embodiment, the number of non-current members proximal to the magnetic electrode is equal to the number of high current components minus one. Moreover, the number of high current components fully merged into the pocket filled with conductive fluid is equal to the sum of magnetic electrode and non-current component proximal to it. This assembly is preferable for electro-magnetic stability of the components and electrochemical stability of the system.

Figure 16:
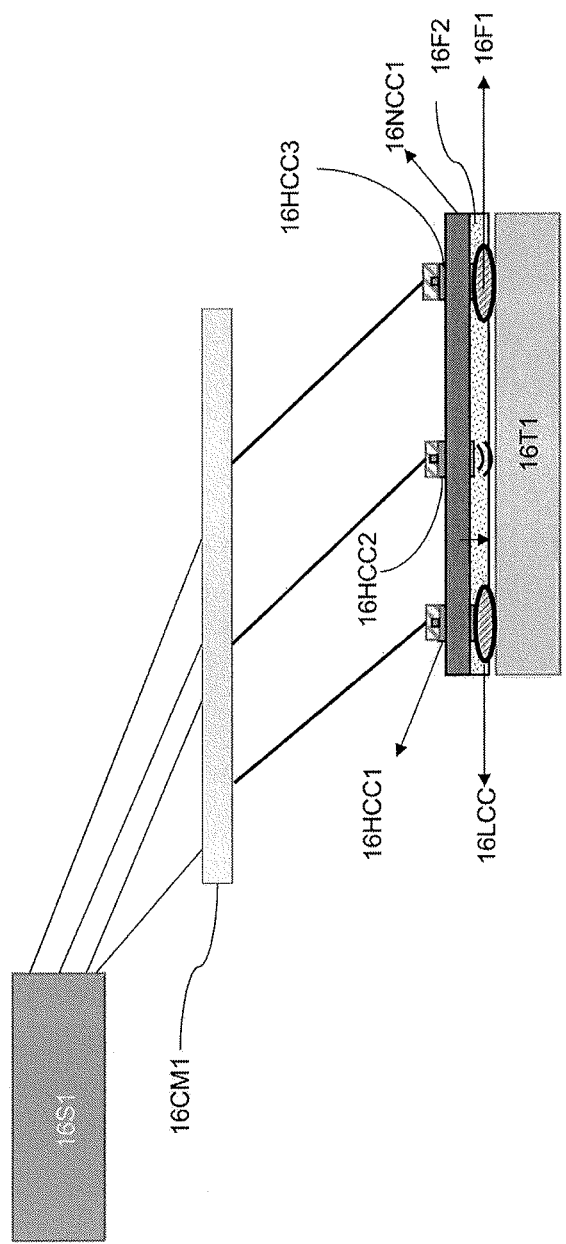
FIG. 16 is a cross-section view of a possible electrode assembly with high current components, non-current member, and low current component.

FIG. 16 represents another embodiment where high current components are in contact with the porous pockets of conductive fluid that are found inside a thin layer of a low current component. High current components are embedded inside the low current component through a layer of non-current member that is attached to it. Both high current components 16HCC1 and 16HCC3 are connected internally to a porous pocket filled with conductive fluid 16F1, whereas externally, they are in contact with a low current component 16NCC1 and are connected to the current leads. The lower section of these porous pockets is in contact with the conductive fluid 16T1. The internal section of one high current component 16HCC2 is suspended in a thin layer of porous pocket that is filled with conductive fluid 16F2 but is not in contact with the tissue 16T1.

In this embodiment, the number of high current components not in contact with the tissue is equal to the number of high current components in contact with the porous pocket of conductive fluid that is in contact with the tissue minus one. This assembly ensures maximum safety, tolerability, and efficacy in neuromodulation.

Figure 17:
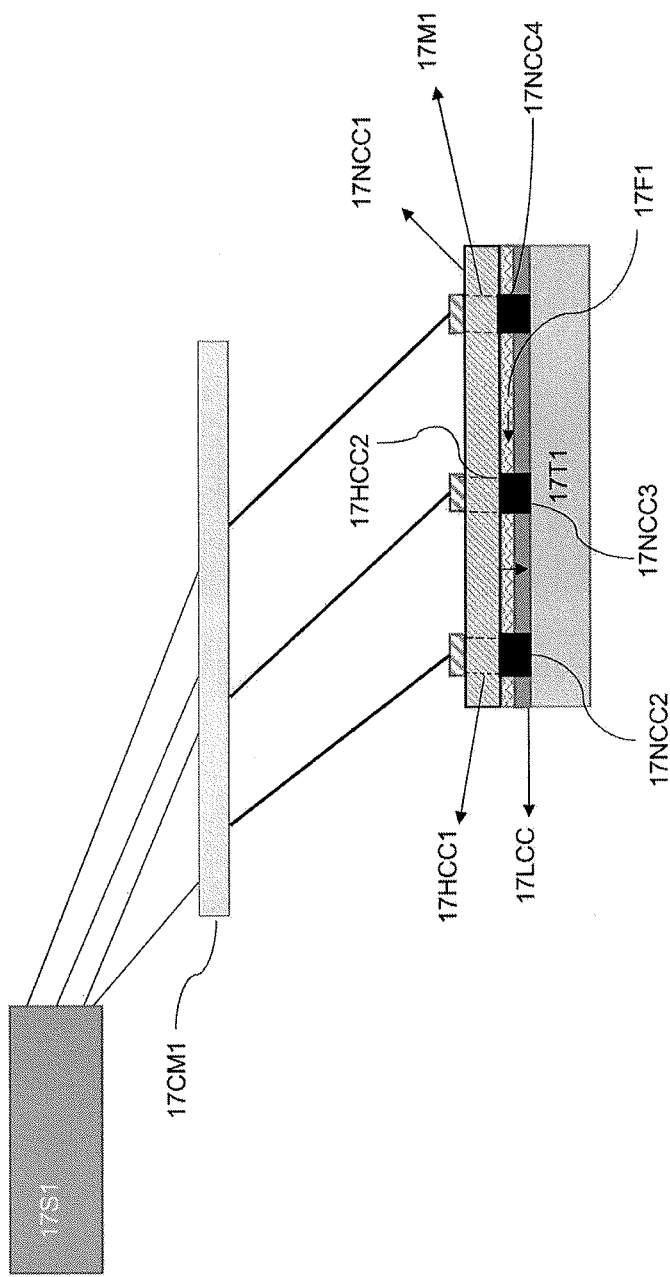
FIG. 17 is another possible example of a cross-section view of electrode assembly with high current components, magnetic electrode, non-current components, and low current component.

FIG. 17 is an illustration of another embodiment where a second non-current member/layer with embedded high current components and magnetic electrodes is placed parallel to the first non-current members that are found inside the low current component and are in contact with the tissue. Here, two high current components 17HCC1, 17HCC2, and a magnetic electrode 17M1 are all embedded inside a non-current component 17NCC1. The lower ends of these two high current components 17HCC1, 17HCC2, as well as a third high current component 17HCC3, protruding out of the non-current component 17NCC1 are respectively in contact with a second 17NCC2, third 17NCC3, and fourth 17NCC4 non-current component. These second, third and fourth non-current components 17NCC2, 17NCC3, and 17NCC4 are merged inside a porous pocket of a low current component 17LCC filled with a conductive fluid 17F1. Together, the first non-current component 17NCC1 with embedded high current components and magnetic electrode, and the low current component 17LCC with conductive fluid and non-current member connections for the corresponding high current component and magnetic electrode, make a single assembly that is in contact with the tissue surface 17T1.

In this embodiment, the number of non-current member in contact with the low current component and surrounded by conductive fluid is equal to the number to the number of magnetic electrode plus high current components. The advantage of this assembly includes safety, electrochemical stability, and uniformity in current density distribution within the components of the assembly.

Figure 18:
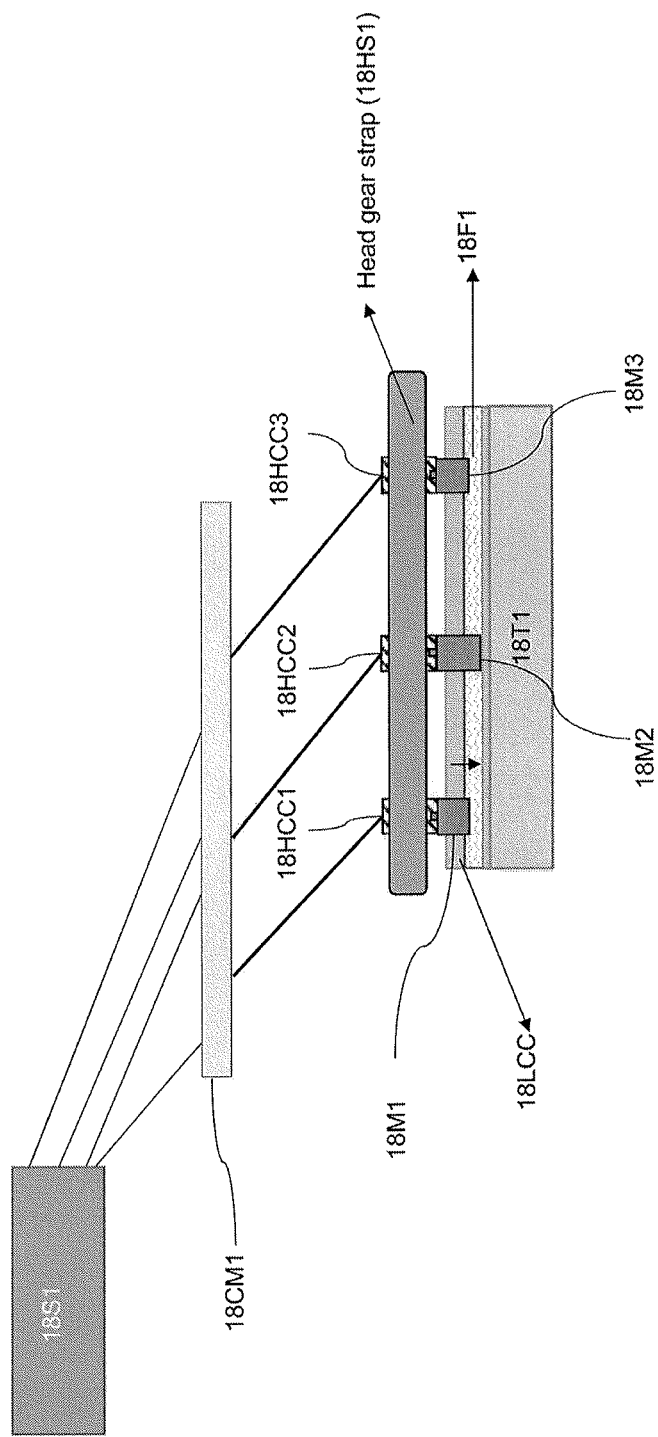
FIG. 18 is a cross-section view of an electro-magnetic apparatus arrangement in a head gear strap with high current components, magnetic electrodes, and low current component.

FIG. 18 is an illustration of another embodiment where high current components are present in a head gear strap and the magnetic electrodes from low current components make secure and rigid connection enabling electro-magnetic induction throughout the low current component. In another embodiment, two magnetic electrodes are suspended in the porous pocket of conductive fluid to control/check the current distribution through in electrode current steering. Three high current components 18HCC1, 18HCC2, and 18HCC3 are embedded in the strap 18HS1 and the lower protruding end of the female/male snap of these high current components are connected to the male/female snap of three magnetic electrodes 18M1, 18M2, and 18M3. The second 18M2 of these three magnetic electrodes is extended all the way through the conductive fluid 18 F1 to the upper layer of a lower section of a low current component 18LCC, whereas the other two magnetic electrodes 18M1 and 18M2 are just in contact with the conductive fluid 18F1. The porous lower section of the low current component 18LCC filled with the conductive fluid 18F1 is in contact with the tissue surface 18T1.

In this embodiment, the number of high current components rigidly connected to magnetic electrodes through a head gear strap is equal to the number of magnetic electrodes that just touch the surface of conductive fluid plus one and is also equal to the number of magnetic electrodes that extend throughout the length of conductive fluid layer to the upper layer of lower section of low current component plus two. This set up helps in maximizing robustness, electro chemical performance, mechanical stability, and effectiveness of the assembly during electrical stimulation.

Figure 19:
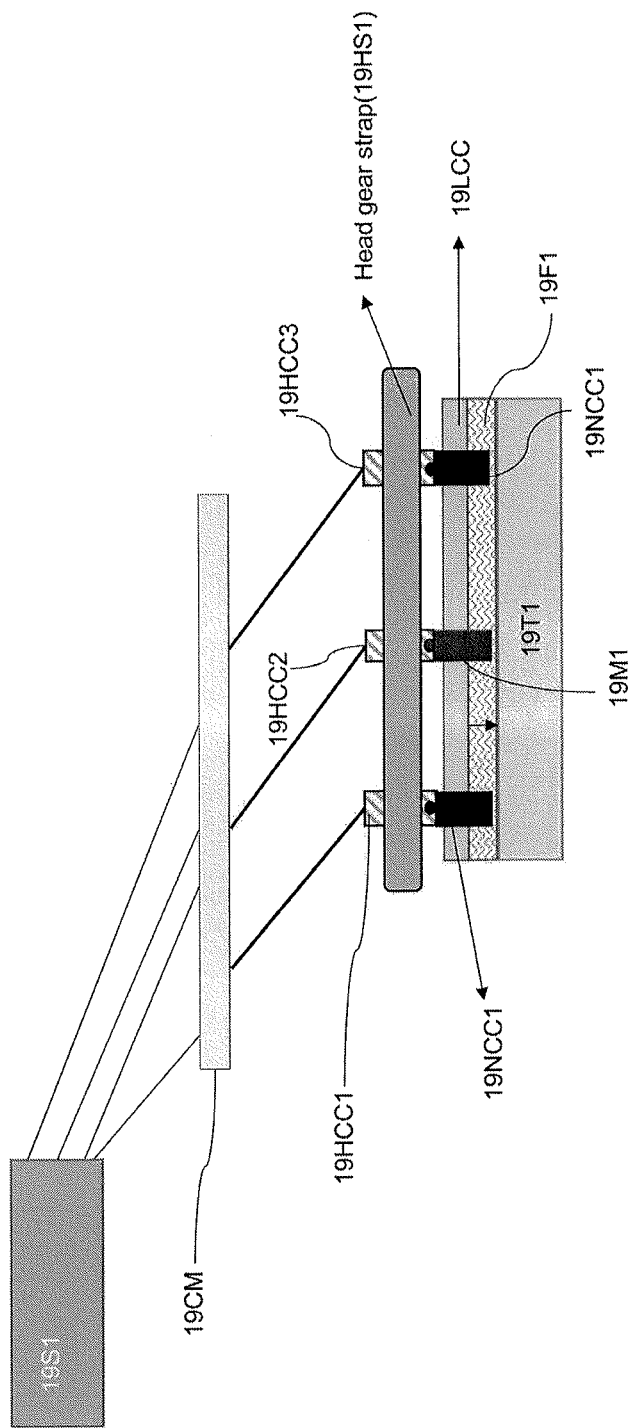
FIG. 19 is another possible example of a cross-section view of an electrode assembly with high current components, non-current members, and low current component.

FIG. 19 is an illustration of another embodiment similar to that shown in FIG. 18 where the high current components from a head gear strap are rigidly connected to non-current members from the lateral ends and magnetic electrode from the middle portion of the low current component but are not contact with the tissue. Here, three high current components 19HCC1, 19HCC2, and 19HCC3 are respectively connected to a non-current component 19NCC1, a magnetic electrode 19M1, and a high current component 19HCC3 through a head strap 19HS1. The non-current component 19NCC1, the magnetic electrode 19M1, and the high current component 19HCC3 are embedded inside a low current component 19LCC and their lower ends are surrounded by conductive fluid 19F1 in a porous pocket. Together, the low current component 19LCC, the conductive fluid 19F1, and the snaps of the non-current component 19NCC1, the magnetic electrode 19M1, and the high current component 19HCC3 make a single assembly. The lower section of this compact assembly is in contact with the tissue surface 19T1.

In this embodiment, the number of magnetic electrodes suspended in the porous pocket of conductive fluid is equal to the number of non-current components connected to the high current components minus one. Moreover, the number of high current components not connected to a magnetic electrode is equal to one more than the ones connected to the magnetic electrode. This system is preferable for mechanical stability of the system and uniform current distribution during rehabilitation of neuropsychological disorders.

Figure 20:
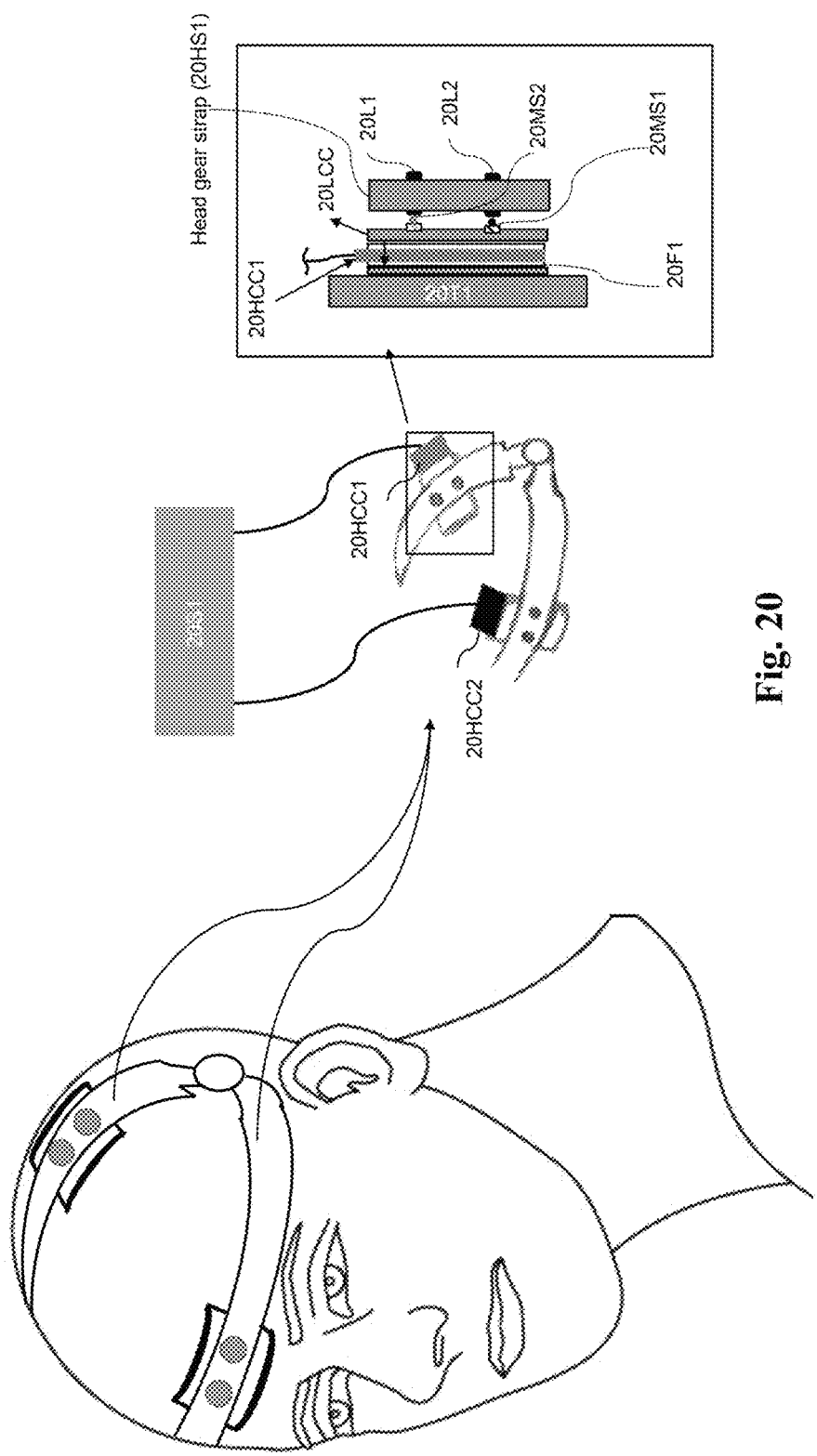
FIG. 20 is another possible example of a perspective and cross-section view of electro-magnetic apparatus arrangement in a head gear strap with high current components, magnetic electrodes, and low current component.

FIG. 20 represents another embodiment where there is a rigid connection between the metal snaps/leads/buttons from head gear strap and magnetic snaps/leads/buttons from the electrode assembly. In another embodiment, a high current component is inserted in between the layers of low current component presoaked with conductive fluid. A high current component 20HCC1 is inside a low current component 20LCC and is surrounded by conductive fluid 20F1, and is also connected to one terminal of a current source 20S 1. The upper section of a low current component 20LCC has two magnetic snaps 20MS1 and 20MS2, which are rigidly connected to metal snaps of respective leads 20L1 and 20L2 of the head gear strap 20HS1. The lower section of the low current component 20LCC is in contact with the tissue surface 20T1.

In this embodiment, the number of high current component found in between the layers of the low current component 20LCC is equal to the number of magnetic snaps connected to the metal snaps of the head gear strap minus one. This system provides maximum mechanical stability due to secure and flexible magnetic and metallic connection. In addition, the electrode assembly enhances uniform current density distribution and hence maximizes skin tolerability during brain stimulation.

Figure 21:
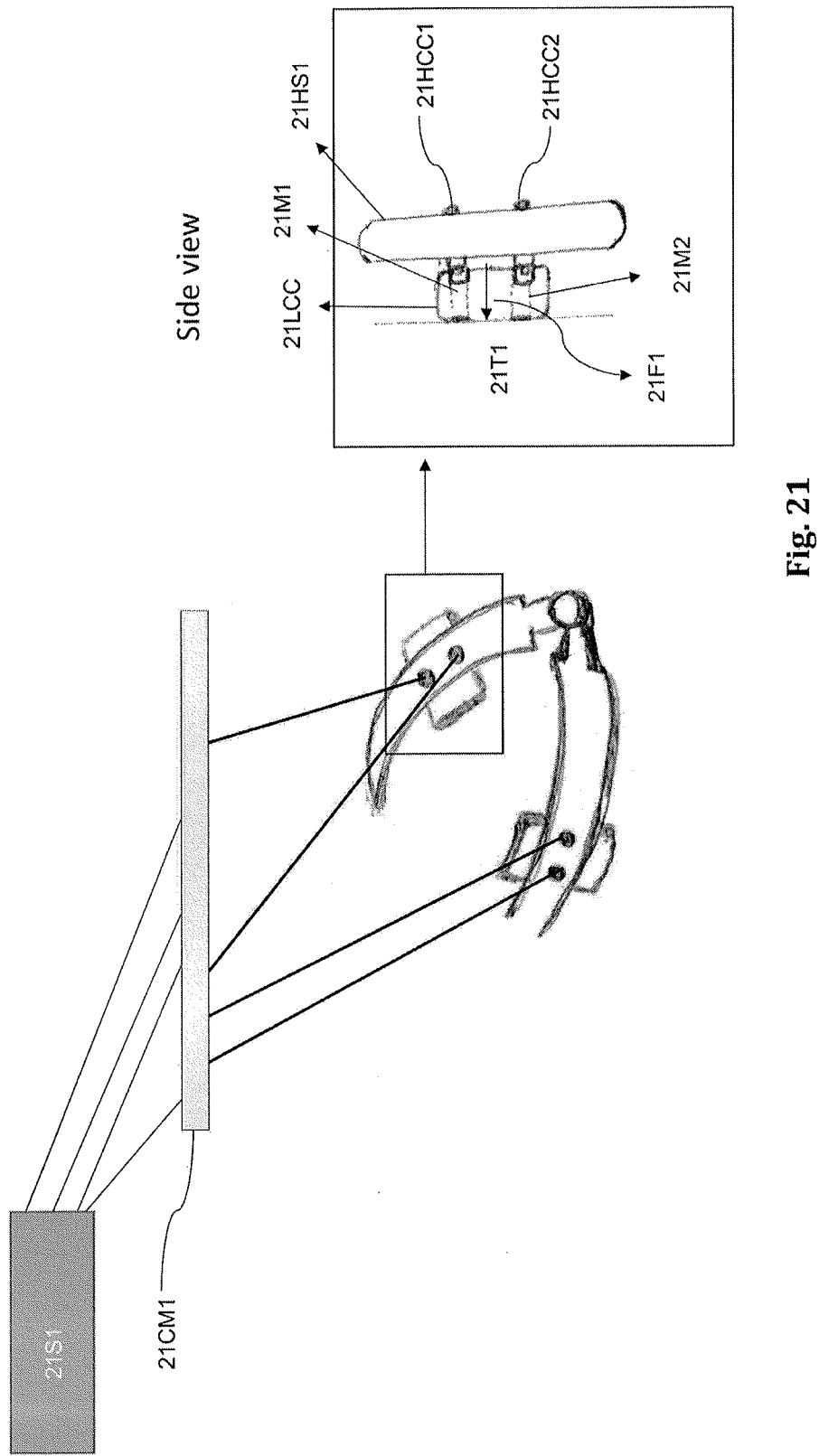
FIG. 21 depicts another possible example of a perspective and cross-section view of an electro-magnetic assembly in a head gear strap with high current components, magnetic electrodes, and low current components.

FIG. 21 is an illustration of another embodiment similar to that shown in FIG. 18 where high current components from a head gear strap are rigidly connected to the magnetic electrodes embedded inside a low current component and are in contact with the lower section of the low current component. Specifically, two high current components 21HCC1 and 21HCC2 are both connected rigidly to respective magnetic electrodes 21M1 and 21M2, which are embedded inside a low current component 21LCC and are surrounded by a conductive fluid 21F1. The upper section of the low current component 21LCC has either a male/female snap that makes secure connection with the corresponding female/male metal snap from the head strap 21HS1. The bottom section of the low current component 21LCC is in contact with the tissue surface 21T1.

In this embodiment, the number of high current components found in the head gear strap is equal to the number of magnetic electrodes embedded inside the low current components. This electro-magnetic apparatus is preferable due to mechanical stability, safety, and convenience of assembly for neuromodulation purposes.

Figure 22:
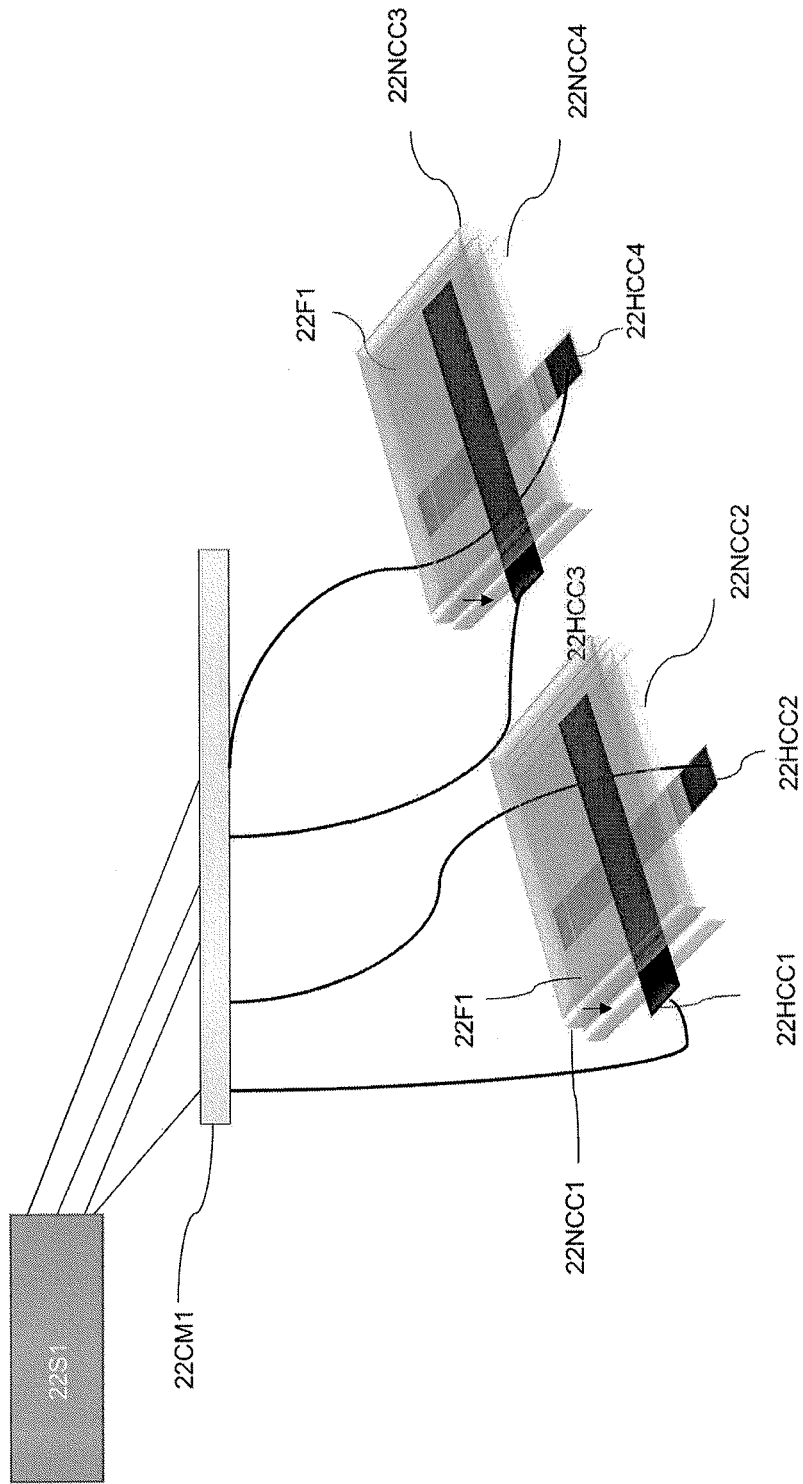
FIG. 22 depicts a perspective view of a possible example of an electrode assembly with high current components arranged in a low current component.

FIG. 22 represents an illustration of another embodiment where two perpendicular compliant high current components are arranged in a low current component in such a way that one of them is on top of a bottom layer of low current component whereas the other one lies on top of a first non-current member (for e.g. PDMS) that is in between the two high current component. In another embodiment, a second non-current component is placed between the conductive fluid and the top high current component to avoid short circuiting. Conductive fluid 22F1 is filled on the top layer of two non-current components 22NCC1 and 22NCC3. Four high current components 22HCC1, 22HCC2, 22HCC3, and 22HCC4 are independently connected to each port of a current multiplexor 22CM1. One high current component 22HCC1 is placed in between two non-current components 22NCC1 and 22NCC2 and another high current component 22HCC3 is placed in between two other non-current components 22NCC3 and 22NCC4. Two high current components 22HCC2 and 22HCC4 are placed at the bottom of the non-current components 22NCC2 and 22NCC4 respectively.

In this embodiment, the number of high current components separated by a first non-current component is equal in each of the assembly. One advantage of this electrode assembly is when a high voltage is applied between the high current components, an electrostatic pressure exists at the intersection of the components which might aid in localizing current to any specific point of interest within the electrode assembly.

Figure 23:
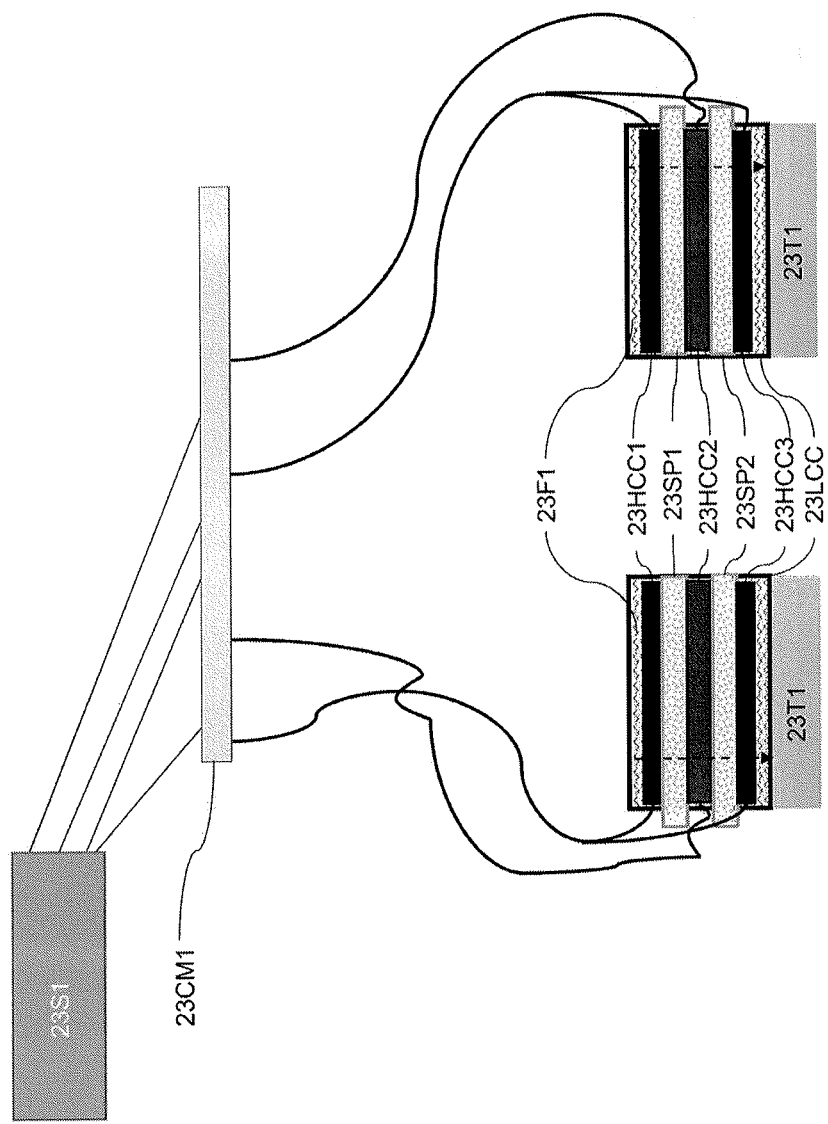
FIG. 23 depicts a cross-section view of another possible example of an electrode assembly with layers of high current components arranged inside a low current component.

FIG. 23 is an illustration of another embodiment where high current components are arranged inside a low current component in layers between porous pockets of conductive fluids. Specifically, a first high current component 23HCC1 is separated from a second high current component 23HCC2 by a porous layer 23SP1. Similarly, the second high current component 23HCC2 is separated from a third high current component 23HCC3 by another porous layer 23SP2. All of these layers 23HCC1, 23SP1, 23HCC2, 23SP2, and 23HCC3 are disposed inside a low current component 23LCC, which is filled with conductive fluid 23F1. The low current component 23LCC is in direct contact with the tissue surface 23T1.

In this embodiment, the number of high current components in each low current component connected to a same port is equal to the number of high current components minus one. This arrangement is preferable due to electrochemical stability.

Figure 24:
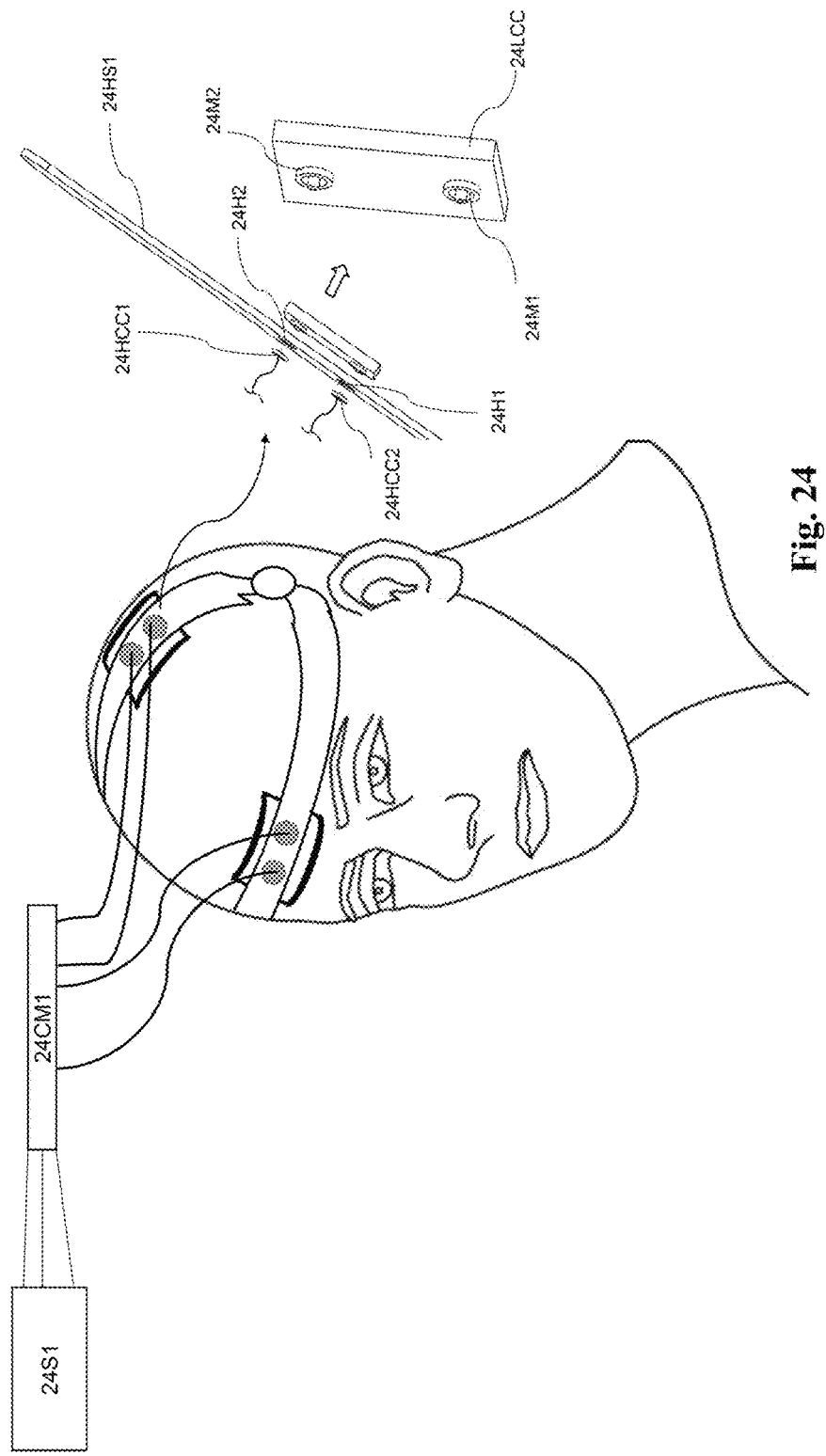
FIG. 24 shows perspective views of another possible example of an electro-magnetic apparatus arrangement in a human head using head gear strap where magnetic electrodes from low current component will be rigidly connected to the high current components of it.

FIG. 24 depicts another illustration of an embodiment similar to that shown in FIG. 18 where two high current components are rigidly connected to the magnetic electrodes of a low current component, and which are all assembled in a headgear strap. Here, two high current components 24HCC1 and 24HCC2 fit inside respective holes 24H1 and 24H2 lined by metal, wherein respective magnetic electrodes 24M1 and 24M2 snap in to make a rigid and compact assembly. These magnetic electrodes 24M1 and 24M2 extend close to the base of a low current component 24LCC and are surrounded by a conductive fluid pocket. This set up is preferable in a sense that it provides maximum mechanical stability and proper skin electrode contact during transcranial electrical stimulation.

Figure 25A:
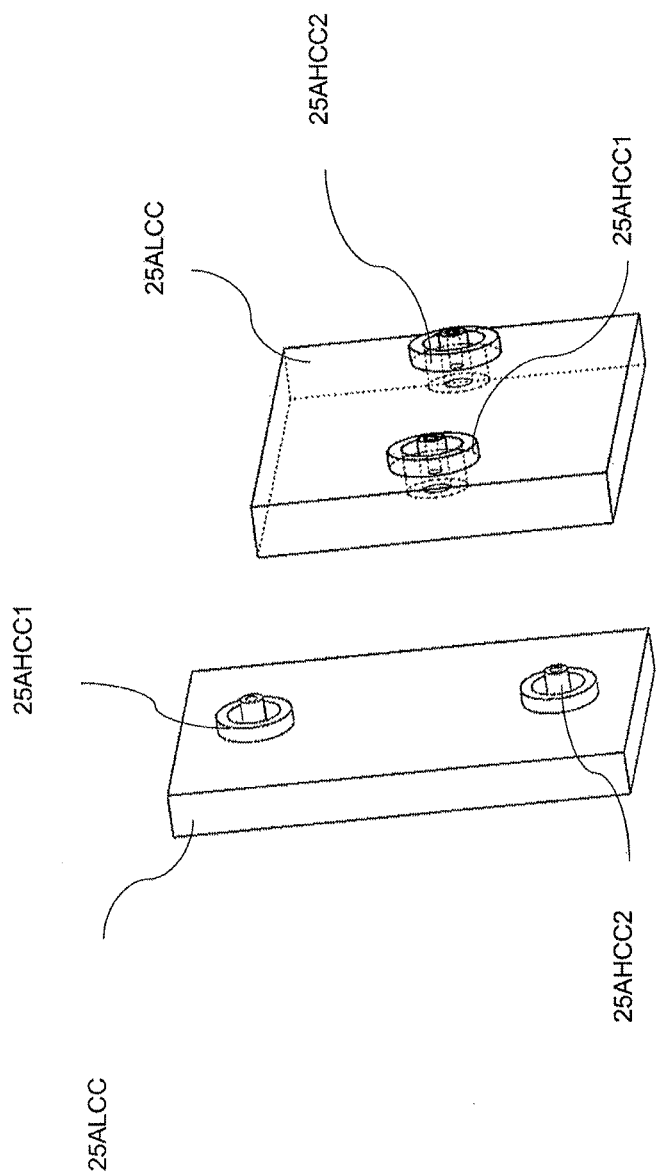
FIG. 25A is another possible example of a perspective view of an electrode assembly with high current components arrangement in a low current component.

FIG. 25A is an illustration of another embodiment where two high current components are arranged in a low current component. The figure shows a perspective view of: high current components 25AHCC1 and 25AHCC2 embedded in a low current component 25ALCC; left and internal schematic of both HCC and LCC as a composite structure; right. This electrode assembly will ensure within electrode current steering during brain stimulation.

Figure 25B:
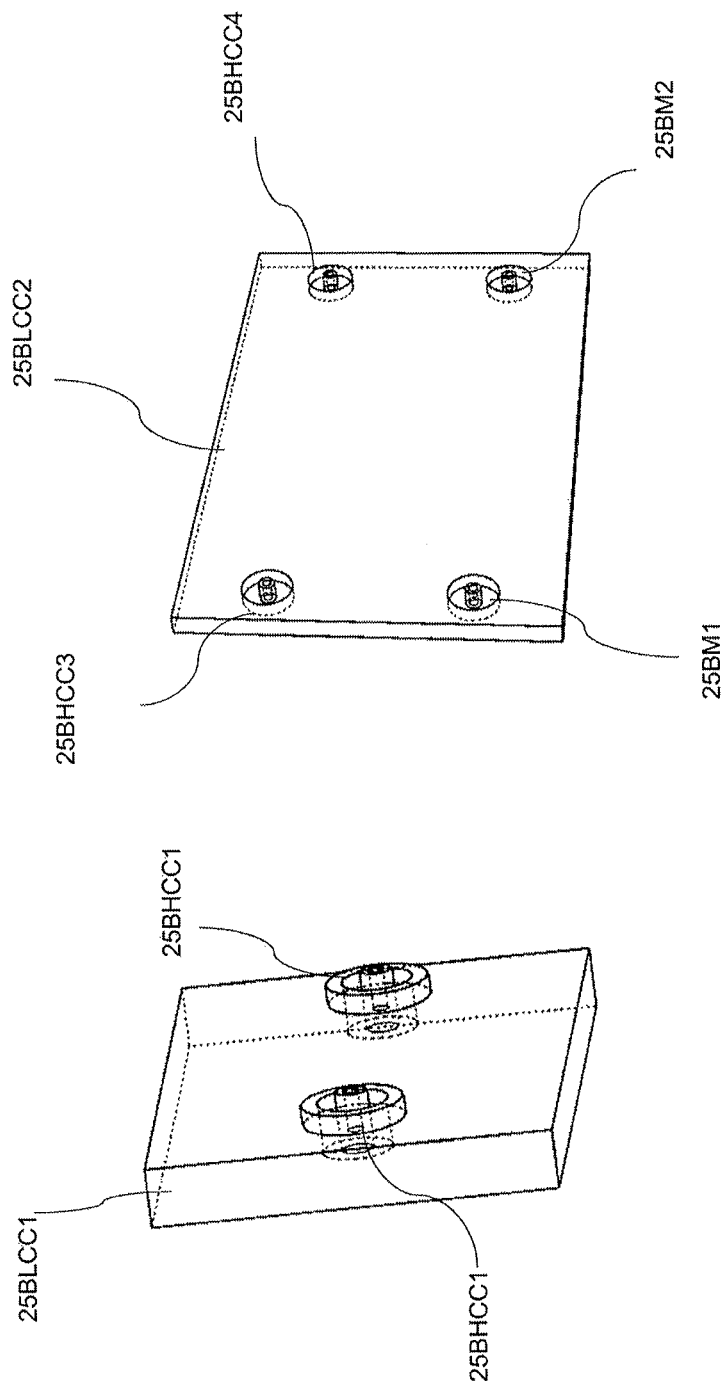
FIG. 25B is another possible example of a perspective view of an electrode assembly with high current components and low current components.

FIG. 25B is another illustration of an embodiment of FIG. 25A with another four high current components arrangement in a low current member. Two of the four high current components 25BHCC1 and 25HCC2 are embedded in a low current component 25BLCC1, as shown in FIG. 25A (left), whereas two magnetic electrodes 25BM1 and 25BM2 and two high current components 25BHCC3 and 25BHCC4 are arranged in the low current component 25BLCC2 in opposite ends (right). This electrode assembly will ensure safety, tolerability, and efficacy in neuromodulation procedures.

Figure 25C:
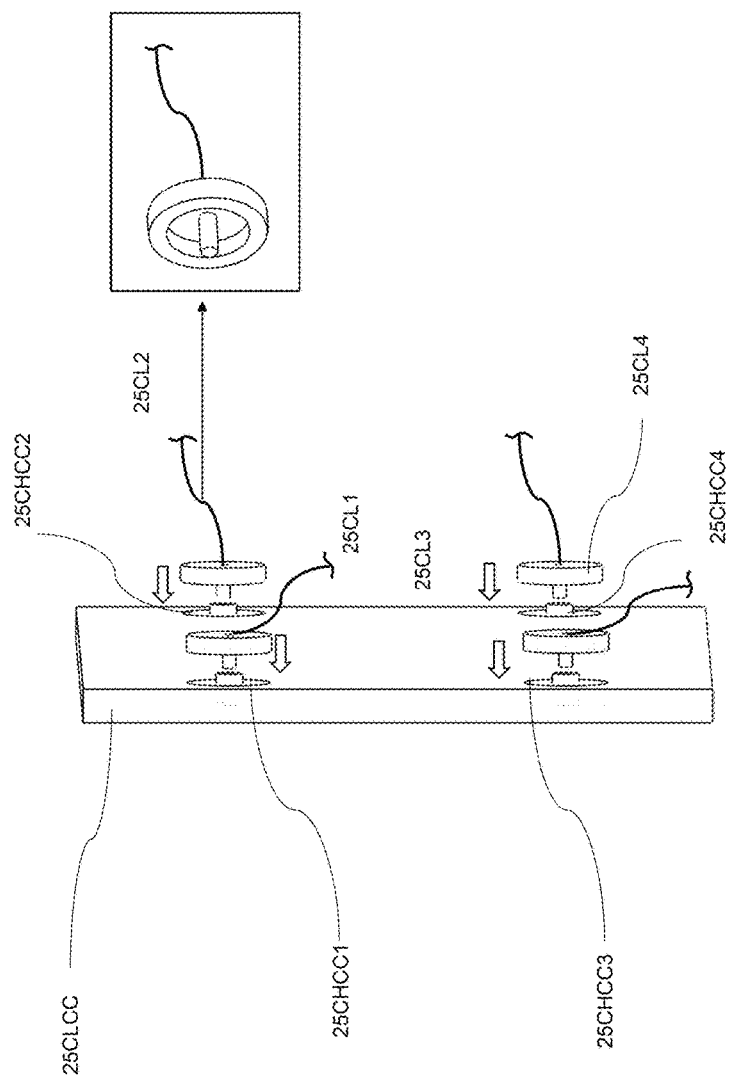
FIG. 25C is a side view of another possible example of an electrode assembly with current leads, high current components, and low current component.

FIG. 25C is another illustration of an embodiment as shown in FIG. 25B with current leads connection with high current components embedded in a low current component. Four leads 25CL1, 25CL2, 25CL3, and 25CL4 are all respectively connected rigidly to high current components 25CHCC1, 25CHCC2, 25CHCC3, and 25CHCC4 that are embedded partially into a low current component 25CLCC and are surrounded by a pocket of conductive fluid. The four leads 25CL1, 25CL2, 25CL3, and 25CL4 may be lined by a magnetic material. This set up ensures mechanical stability and might maximize electro-magnetic induction during stimulation.

Figure 26A:
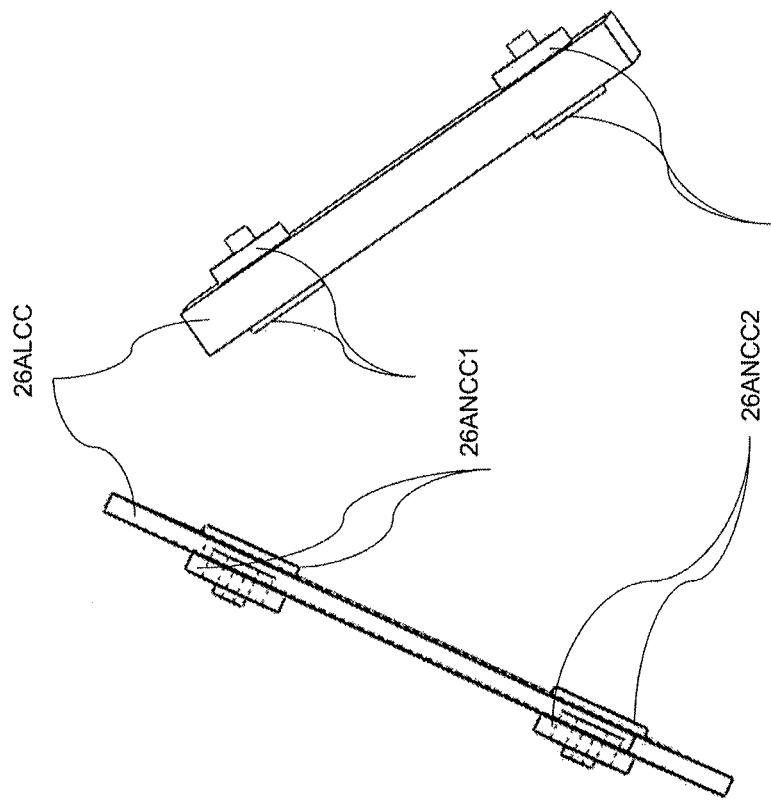
FIG. 26A depicts a cross section and a side view of possible example of an electrode assembly with non-current members and low current component.

FIG. 26A is another illustration of an embodiment mentioned earlier in FIG. 25A where the high current components are replaced with non-current members. Thus, two non-current components 26ANCC1 and 26ANCC2 are positioned in a low current component 26ALCC in such a way that their top and bottom ends are exposed out of the low current component 26ALCC. This electrode assembly increases safety and tolerability while maintaining uniform current density distribution within electrodes.

Figure 26B:
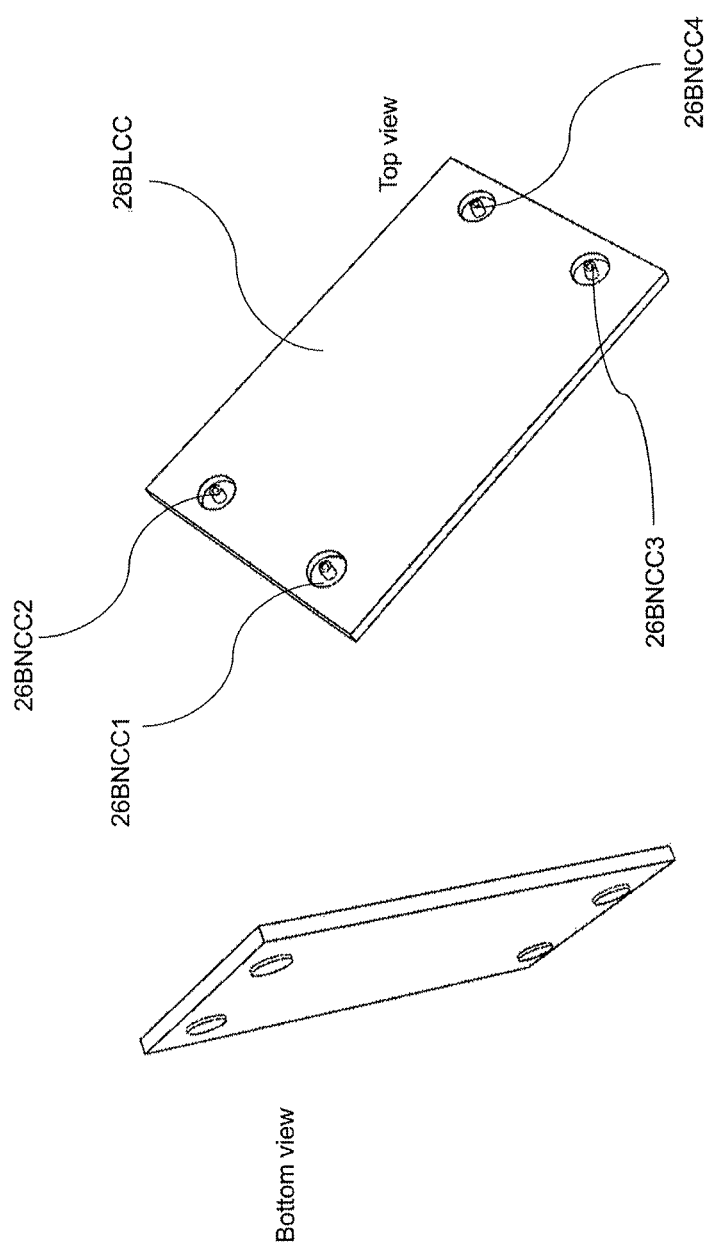
FIG. 26B shows perspective views of another possible example of an electrode assembly with non-current members and low current component.

FIG. 26B is another illustration of an embodiment as mentioned in FIG. 25B where the high current components are replaced by non-current members. Thus, four non-current members 26BNCC1, 26BNCC2, 26BNCC3, and 26BNCC4 are arranged around the corner edges of a low current component 26BLCC. This kind of assembly provides maximum safety, increases efficacy and reliability of the system for brain modulation.

FIG. 26C is another illustration of the embodiment previously mentioned in FIGS. 25B and 25C where the high current components of FIG. 25C are replaced by non-current members. Current leads 26CL1, 26CL2, 26CL3, and 26CL4 are connected rigidly to respective non-current components 26CNCC1, 26CNCC2, 26CNCC3, and 26CNCC4. In this case, current density is uniformly distributed across the low current component.

Figure 27A:
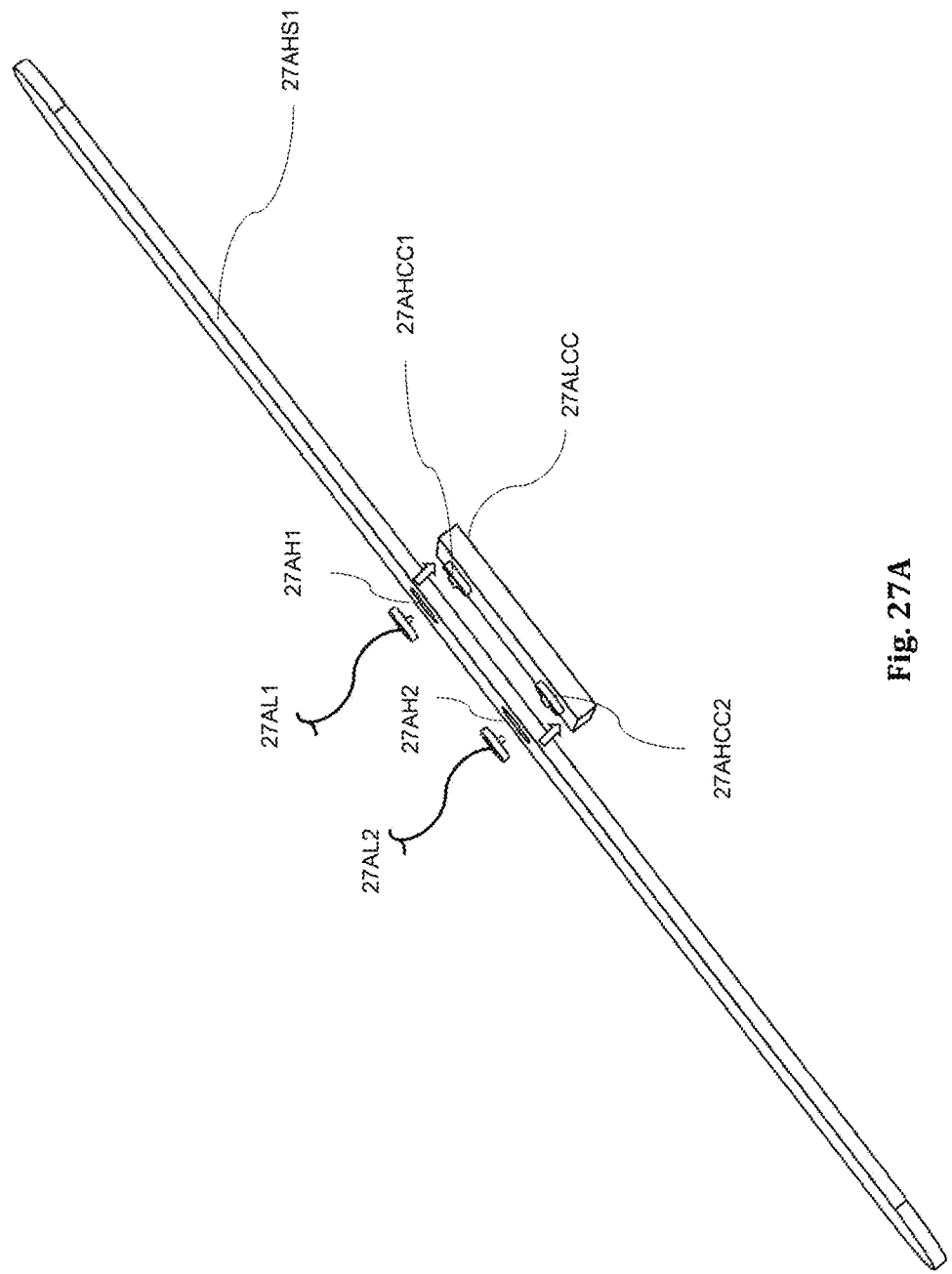
FIG. 27A is another example of a possible perspective view of an electrode assembly in a head gear strap with current leads, high current components, and low current component.

FIG. 27A is an illustration of another embodiment where the high current components and current leads are connected to each other through a magnetic lining found in the ports of a head gear strap. Two leads 27AL1 and 27AL2 go through holes 27AH1 and 27AH2 of the head strap 27AHS 1 and are connected to respective high current components 27AHCC1 and 27HCC2. Parts of the high current components 27AHCC1 and 27AHCC2 are embedded into a low current component 27ALCC and are surrounded either by a pocket of conductive fluid or in contact with the presoaked surface of the low current component 27ALCC. This set up ensures mechanical stability and robustness of the assembly.

Figure 27B:
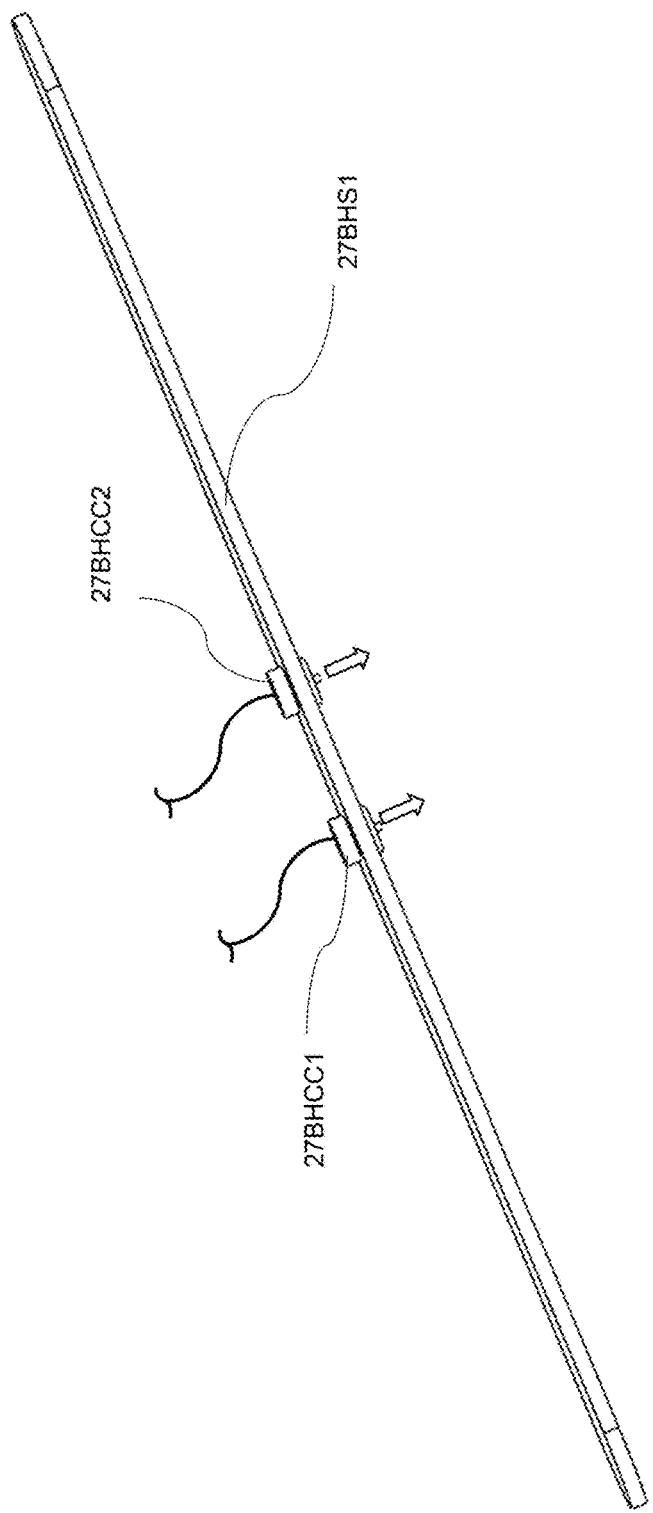
FIG. 27B depicts perspective view of another possible example of an assembly where high current components are pre-arranged in a head gear strap.

FIG. 27B is an illustration of another embodiment where the head gear strap components are prebuilt with high current components. The male/female snap of the high current components 27BHCC1 and 27BHCC2 may be connected to either female/male snap of another high current component, magnetic electrode or non-current member. This assembly aids in maximizing mechanical stability and increasing safety during transcranial direct current stimulation (tDCS).

Figure 28A:
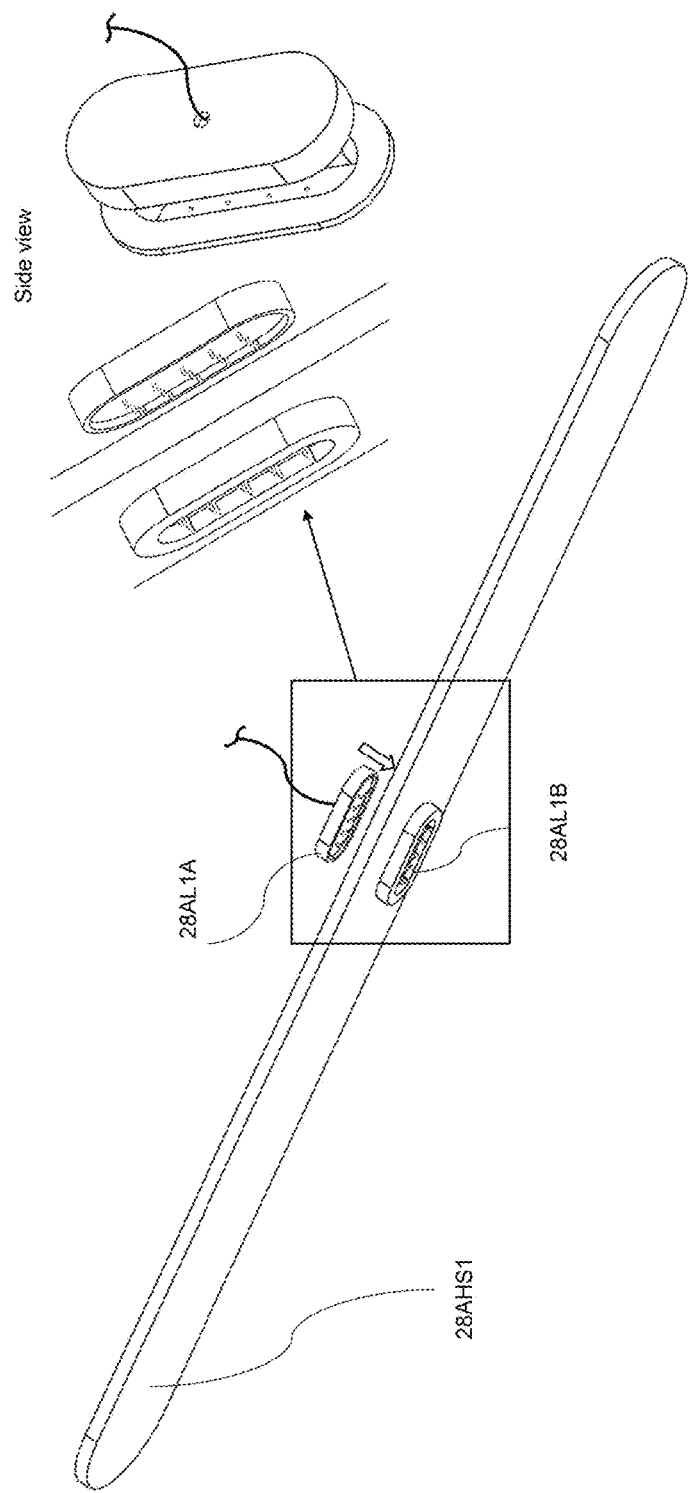
FIG. 28A shows another example of a possible perspective views of current leads assembly in a head gear strap.

FIG. 28A is an illustration of another embodiment where the current leads have corresponding built in ports (either lined with/without magnet) in a head gear strap. 28AL1B of 28AHS1 may be connected to either a male or female magnetic port present in the top layer of any low current component. Together they will make a rigid assembly. Some advantages of this assembly include mechanical stability, rigid connection, electrical safety, and maximum tolerability during stimulation.

Figure 28B:
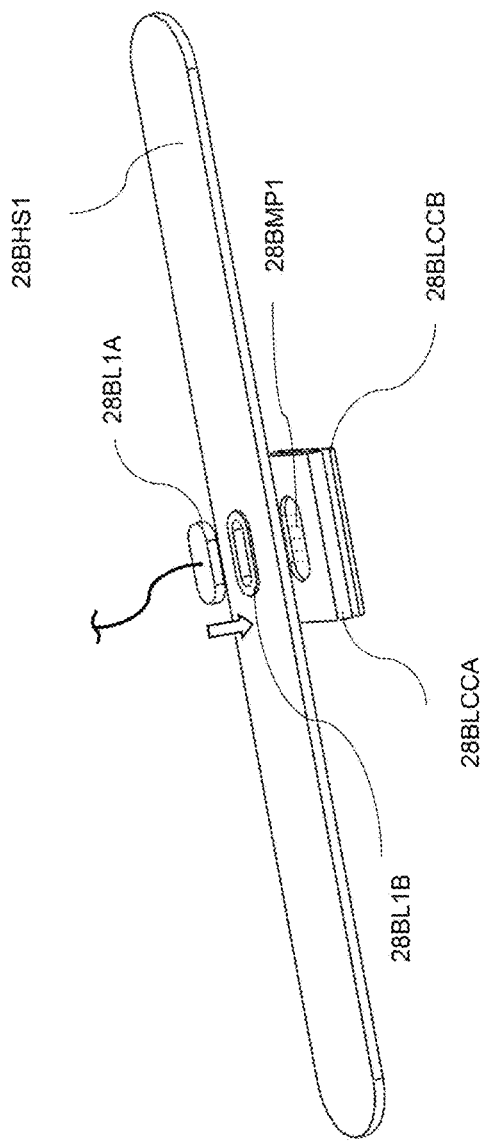
FIG. 28B is another example of a possible perspective view of an electrode assembly in a head gear strap with current leads and magnetic ports from low current component.

FIG. 28B is another illustration of an embodiment mentioned in FIG. 28A with a low current component having magnetic ports. 28BL1A is connected to 28BL1B whose lower end is further connected to the magnetic port (28BMP1) of 28BLCCA. 28LCCA might have either high current components or non-current members embedded within it which might be further extended through out or to a section of 28BLCCB. The gap in between 28LCCA and 28BLCCB may be filled with a conductive fluid or they may be presoaked. This assembly maximized mechanical and electrical stability while ensuring robustness of the set up.

Figure 28C:
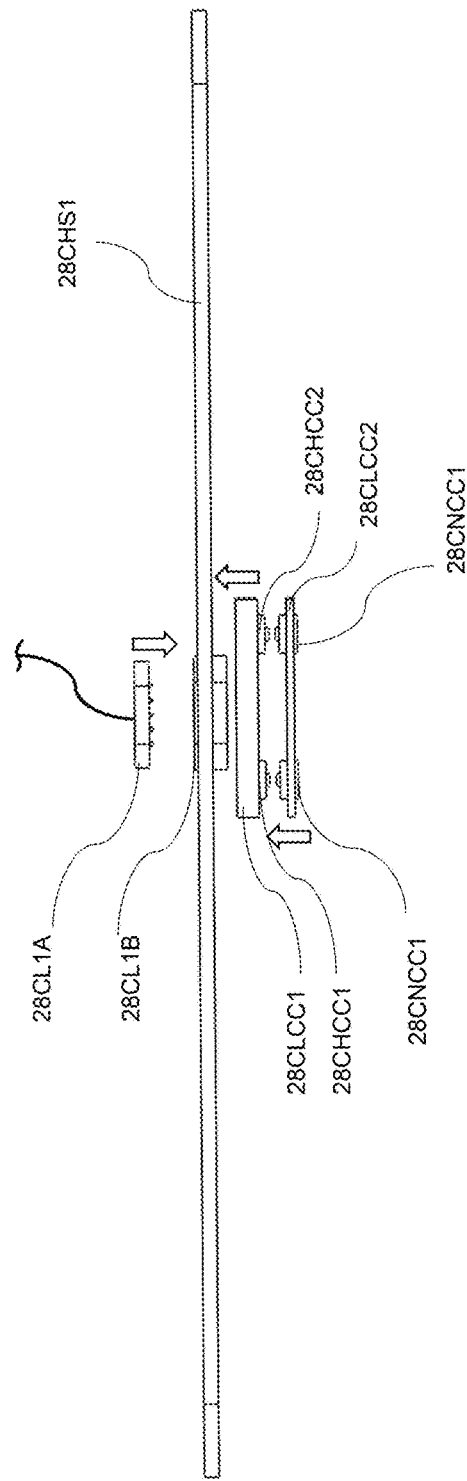
FIG. 28C depicts a side view of another possible example of an electrode assembly in a head gear strap with current lead, high current component, non-current members, and low current component.

FIG. 28C is another illustration of an embodiment mentioned in FIG. 28A with a top layer of low current component (connected rigidly to the port of head gear strap) having protruding high current components rigidly connected to the respective non-current members from another layer of low current component. Male/female snap of a first lead 28CL1A is connected to female/male snap of a second lead 28CL1B of the head strap 28CHS 1. Port of a low current component 28CLCC 1 is connected to the lower port of 28CL1B. Two high current components 28CHCC1 and 28CHCC2 from the low current component 28CLCC1 are connected to non-current components 28CNCC1 and 28CNCC2 of the low current component 28CLCC2. This electrode assembly ensures mechanical stability and within electrode current steering.

Figure 28D:
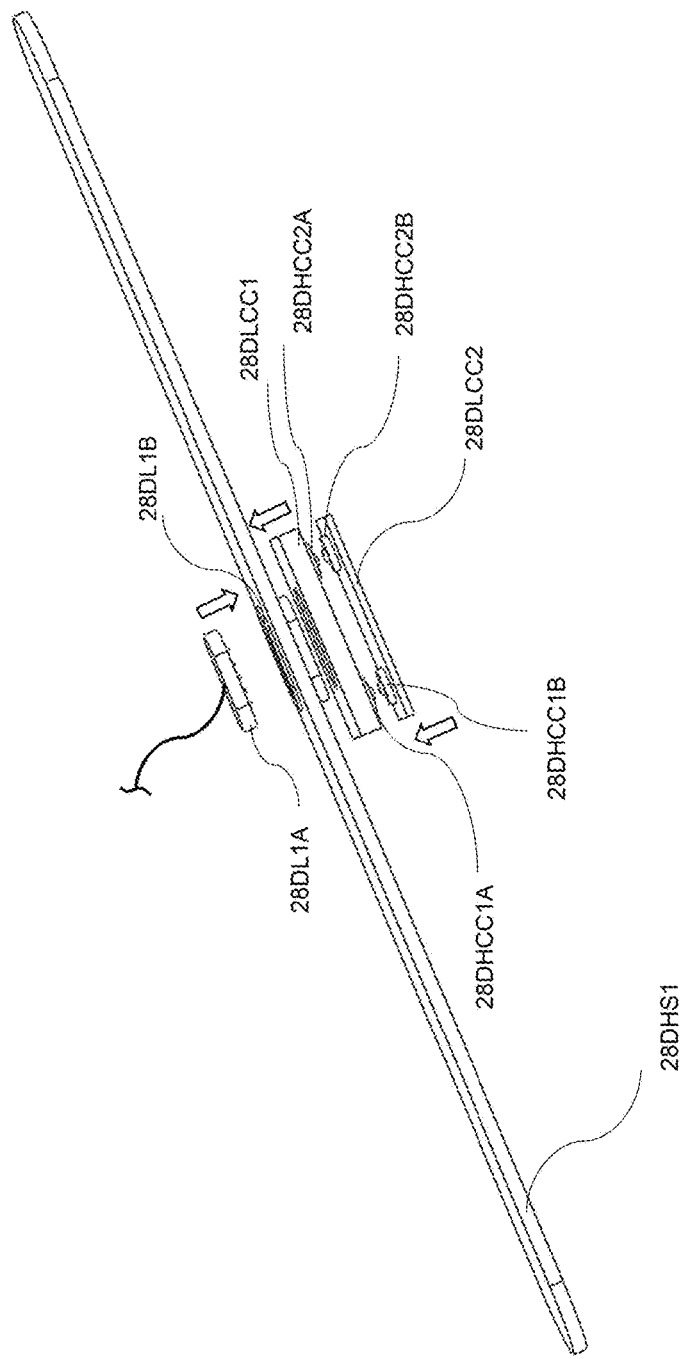
FIG. 28D shows another example of a possible perspective view of an electrode assembly in a head gear with current leads, high current components, and low current component.

FIG. 28D depicts another illustration of an embodiment mentioned in FIGS. 28A and 28C with a top layer of low current component having protruding high current components are connected to the respective high current component present in another layer of low current component. Male/female snap of a first lead 28DL1A is connected to female/male snap of a second lead 28DL1B of head strap 28DHS 1. Port of the low current component 28DLCC1 is connected to the lower port of the second lead 28DL1B. Two high current components 28DHCC1A and 28DHCC2A from the low current component 28DLCC1 are connected to high current components 28DHCC1B and 28DHCC2B of 28DLCC2. This system aids in maximizing mechanical and electrochemical stability while ensuring robustness of the assembly.

Figure 28E:
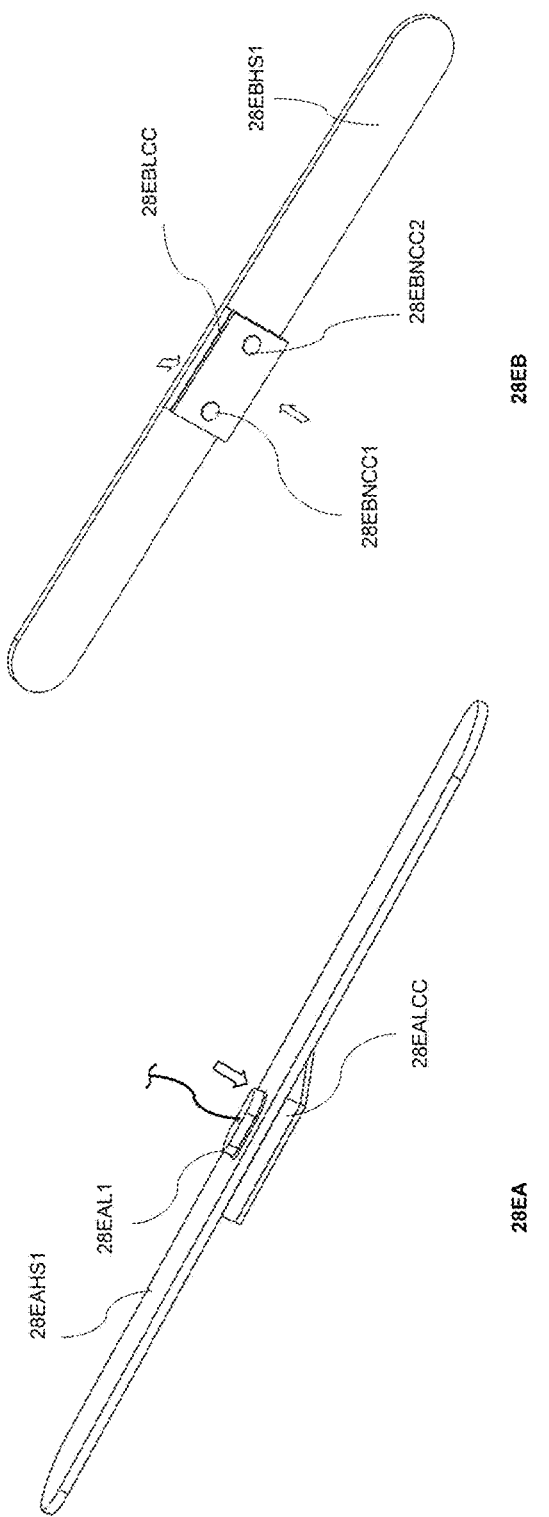
FIG. 28E is another example of a possible perspective views of an electrode assembly in a head gear strap with current lead, high current components (28EA), non-current members (28EB), and low current component.

FIG. 28E shows another illustration of an embodiment mentioned in FIG. 28D with a low current component with high current component or non-current member connected to the ports of head gear strap and then to the current lead.

28EA, 28EAL1 is connected to the port of 28EAHS1 and the bottom port of 28EAHS1 is connected to either magnetic port or magnetic material port of 28EALCC. 28EALCC have embedded high current components surrounded by a pocket of conductive fluid. In 28EB, the current lead/wire might be connected to the top section of 28EBHS1. The bottom port of 28EBHS1 might be connected rigidly to 28EBLCC by means of a magnetic material present around the port present on the top layer of 28EBLCC. 28EBNCC1 and 28EBNCC2 are protruding out of 28EBLCC which are surrounded by conductive fluid inside 28EBLCC. This assembly ensures maximum mechanical stability, reliability, and desirable electrochemical performance of the system during tDCS.

In a preferred environment, where any possible hazardous electrochemical byproducts can be eliminated, the present invention is best implemented when the LCC has a depth less than 5 cm but more than 0.5 cm, most preferably between 0.5-3 cm to the top surface of the tissue in contact. In another embodiment, maximum uniform current distribution can be achieved when one LCC is positioned less than 6 inches and more than 4 inches, preferably within 4-5 inches distance away from another LCC on top of the tissue has both length and width less than or equal to 7 cm, preferably between 2-7 cm. The shape and dimension of the M component vary depending upon either NCC or HCC corresponding component of the assembly environment with which it will make a snap connection.

The thickness of both HCC and NCC is less than half the depth of the LCC, most preferably between 0.1-1 cm to avoid any transient skin effects associated with the proximity between the tissue and the HCC when electrical stimulation is carried out. In certain embodiments, the depth of such M component of the assembly to deliver maximum current to the tissue is less than or equal to the depth of the HCC, preferably about one third the depth of the HCC. The LCC is configured in a particular way that the pocket inside it has an electrically conductive fluid (for e.g. saline, etc.) of thickness equal to or twice the depth of either HCC or NCC. In some embodiments, the spacing between the fluid inside the pocket and the bottom surface of either the HCC or the NCC is greater than twice the depth of the M component of the assembly to enhance safety and tolerability of the current stimulation treatment. In yet another embodiment, the minimum distance between the M component and the NCC component is less than 2 cm but greater than 0.1 cm, preferably 0.1-0.5 cm.

In certain embodiments, the minimum distance between the top surface of the M component and the bottom surface is less than 2 cm but more than 0.1 cm, most preferably between 0.5-1 cm to enhance maximum current distribution through the LCC compartment and eventually to the tissue surface. In one embodiment, the minimum separation between the HCC and the NCC within a conductive fluid pocket is less than twice the depth of the M component. In other embodiments, the minimum distance between two HCC or M components positioned on the same side on the top surface of LCC is less than 7 cm but greater than 3 cm, preferably between 3-5 cm to enhance current delivery through these components while keeping the net current intensity constant throughout the stimulation. In yet some other embodiments, the minimum diagonal distance between either two HCC or M components of the assembly on or within the LCC component is greater than five times or less than seven times the diagonal length or diameter of either HCC or M component, most preferably within five to six times the diagonal length or the diameter of either the HCC or the NCC. In few embodiments, the diameter and diagonal length of either the HCC or the NCC is greater than 8 mm but less than 3 cm, most preferably between 8 mm-2 cm. In yet another embodiment, the minimum distance between male to female snap of either M and HCC combination, HCC and NCC combination, HCC and HCC combination, M and M combination, M and NCC combination or NCC and NCC combination is greater than 0.05 cm and less than 2 cm, most preferably between 0.05-1 cm to ensure rigid contact and hence increase the efficacy of current delivery. It is preferred for the M, HCC, and NCC components to have a regular definite shape but the other irregular shapes are also acceptable if they satisfy maximum and uniform current delivery and distribution to the tissue.

Preferably, the NCC components are composed of materials that are bio-compatible (good for applications that requires skin contact) and offer high dimensional and structural stability under chemical, thermal, electrical and mechanical interactions. Some of these materials include polycarbonate, polyvinylchloride, polyethylene, polytetrafluoroethylene, polyethersulfone, polyetherimide, polyehteretherketone, polypropylene, etc. It is preferred that the NCC component has very good resistance to the conductive fluid and offer good electrical insulation. The resistivity of NCC component is less than $10^{18}$ Ω·cm and greater than $10^8$ Ω·cm, preferably between $10^9$-$10^{16}$ Ω·cm. Thermal conductivity of NCC is less than 0.8 W/(m*K) and greater than 0.25 W/(m*K), most preferably between 0.25 to 0.59 W/(m*K). In this invention, the application of a preferred environment is best represented when the adjacent current flowing through the adjacent M or the HCC component is completely prevented or minimized the level where the underlying tissue directly under the NCC is not affected by the intensity of current flowing through either the M or the HCC component.

In yet other embodiments, the conductive fluid is stable at room temperature and less or no reactive under an electric field. Preferably, the conductive fluid has a conductivity less than 3.5 S/m and greater than 0.05 S/m, preferably between 0.1-2 S/m. Minimum thermal conductivity of such fluid is one tenth times less than the lower preferred value of the electrical conductivity and maximum thermal conductivity is five times the minimum thermal conductivity, preferred between 0.01-0.04 W/m° C. to ensure good skin-electrode contact and enhance neuromodulation.

In most of the embodiments, the LCC component is made out of significantly porous materials (for example, porous silicon (P—Si)), Poly (1-lactic acid)) where the HCC, the NCC, the M components are coupled in any possible fashion via a snap and are in contact with the conductive fluid to deliver current on the tissue for treating neuropsychological disorders. In few implementations, the porous material used in LCC provides significant passage for uniform current delivery from either the HCC or the M for electrical or electromagnetic stimulation during neurostimulation treatment. It is preferred that the conductive fluid filled in the porous pocket of the LCC is uniformly distributed throughout the LCC for better skin-electrode contact required for better current flow through the skin.

In few other implementations, the M component is composed of magnetic materials like ferrite, samarium cobalt, alnico, neodymium iron boron, etc. In certain embodiments, the electrical resistivity of the material is less than $165 \times 10^{-6}$ Ω·cm and greater than $4 \times 10^{-6}$ Ω·cm, preferably between $5 \times 10^{-6}$-$68 \times 10^{-6}$ Ω·cm. In some implementations, the magnetic filed strength of the M component material is greater than 0.5 Nm/A (tesla, T) and less than 2 Nm/A (Tesla (T)), ideally in between 1-1.5 Tesla is desirable for the best implementation of the assembled environment and hence maximize current delivery to the desired tissue.

In certain embodiments, the HCC component material are electrically conductive metals like Copper, Gold, Brass, Tin, Lead, Silver, Zinc, Bronze, etc. The electrical resistivity of the HCC component is less than $100 \times 10^{-9}$ Ω·m and greater than $10 \times 10^{-9}$ Ω·m, desirable between $16 \times 10^{-9}$-$70 \times 10^{-9}$ Ω·m to maximize neurostimulation outcome.

Preferably, the modulus of elasticity of the M component is greater than $18 \times 10^6$ psi and less than $24 \times 10^6$ psi, most preferably between $22 \times 10^6$-$23 \times 10^6$ psi. In yet another embodiment, the ultimate tensile strength of the M component is less than $1/(3 \times 10^3)$ times and greater than $1/(2 \times 10^3)$ times the modulus of elasticity of the M component. The maximum density of the M component is 0.8 higher than the minimum value which is 7.4 g/cc. For the best implementation of the suggested environment, the recoil permeability of the M component must be less than 1.2 but greater than 1, most preferably between 0.98-1.05.

In some embodiments, the viscosity of the conductive fluid (F) is less than $6 \times 10^7$ centipoise (cP) and greater than $1 \times 10^5$ cP, desirable range is between $2 \times 10^5$-$5 \times 10^7$ cP. The pore density of the porous element of the LCC component is less than 25/cm$^2$ but greater than 5/cm$^2$, preferably between 10-20/cm$^2$.

In a preferred embodiment, the young's modulus of the HCC components is less than 200 Gega Pascal (GPa) and greater than 10 GPa, most preferably between 8-180 GPa. The preferred environment is best implemented when the ductility of the HCC is between 7 mm to 70 mm. In yet another implementation, the yield strength of the HCC component is less than 565 Mega Pascal (MPa) and greater than 5 MPa, desirable within 6-550 MPa for maximum structural and dimensional stability. In other embodiment, the lower range of shear for the HCC is twice as high as the lower range of yield strength of the HCC and the upper range of the shear is about 1/10 times as much as the upper yield strength value. In another implementation, the tensile strength of the HCC component is less than 655 MPa and greater than 90 MPa, preferable in between 95-650 MPa. It is preferred that the HCC component is made out of Tin (Sn) but the surface roughness for proposed invention is between 0.025-50 mm. In yet another implementation, the melting point of the HCC is between 180-250° C. to withstand joule heating generated during current delivery to the tissue. In few other embodiments, the thermal expansion coefficient of the HCC component is greater than $1 \times 10^{-6}$/K and less than $50 \times 10^{-6}$/K, most preferably between $2 \times 10^{-6}$-$45 \times 10^{-6}$/K. The density of the HCC is preferable for the best implementation of the proposed environment when it is between 2000-10000 Kg/m$^3$.

Preferably, the ultimate tensile strength of the NCC component is greater than 40 MPa and less than 120 MPa, preferable between 45-110 MPa. Tensile modulus of the NCC component is less than 12 GPa and greater than 0.2 GPa, desirable between 0.2-10 GPa for stability. The Shore A hardness of the NCC component is between 10-100. In yet another implementation, the density is less than 5 g/cm$^3$ and greater than 0.4 g/cm$^3$, most preferably in between 0.5-3 g/cm$^3$. It is preferred for the NCC to have a surface roughness minimized between 0.0010 mm from 0.010 mm for better assembly design of the proposed invention.

In other embodiments, the HCC & the M or the HCC (male) & HCC (female), or other possible combinations of either of the HCC, M, or NCC, is connected as a snap. The bottom layer of the LCC in another embodiment has a sticky patch to control any unexpected conductive fluid leakage before the neurostimulation is carried out or the proposed assembly is placed on top of the tissue. In another embodiment, the HCC or the M or the NCC component form a snap connection with the customized strap. It is preferred the snap is made out of novel elements like gold but the roughness is increased by ten times for highly optimal connection.

In another embodiment, the bottom surface of the HCC is sealed with an insulating element when not in contact with the NCC component but in contact with the conductive fluid pocket to minimize the possible skin effects related to the proximity of the active HCC and the tissue. In few other implementations, the electric leads connecting either the HCC or the M component to the multiplexor and the neurostimulation device's port are embedded inside a composite strap but are isolated from each other. Together the HCC, the M, the LCC, the embedded electric leads, and the NCC components make a single unit of electrode assembly for neuro-electrical stimulation. In another embodiment, the two LCC components are connected to their distal end through a flexible NCC component. This flexible NCC component wraps the LCC around with only exposed M, or HCC component at the top surface of the LCC. In yet another embodiment, the perforated bottom of the LCC component has a network of micro HCC elements. Each of those nodes is further connected to an external circuit of combined current amplifier to monitor real-time current delivery from the neurostimulation device to the tissue.

In most of the implementations, the preferred environment is best implemented when the electrode assembly has less or no edge effect (peak current densities around the edges of the bottom section of the LCC. In another embodiment, the HCC is embedded or sandwiched in the LCC within the conductive fluid pocket for uniform current distribution. In yet another particular implementation, the electrical conductivities of the HCC, the M, and the conductive fluid (F) match to make current delivery focal during neuro-electrical stimulation.

In yet another embodiment, the current density is greater than 15 $\mu A/cm^2$ and less than 2 $A/m^2$, mostly accepted in between 17 $\mu A/cm^2$-1 $A/m^2$. In another implementation for maximum current delivery to the tissue, the magnetic field generated within the final preferred environment is greater than 4 milliTesla (mT) and less than 50 mT, preferably within 5-44 mT.

While various embodiments of the present invention are specifically illustrated and/or described herein, it will be appreciated that modifications and variations of the present invention may be effected by those skilled in the art without departing from the spirit and intended scope of the invention.

What is claimed is:

1. An apparatus for delivering therapeutic electrostimulation across a tissue surface, the apparatus comprising:
    a current source;
    a low current component adapted to contact the tissue surface;
    a first electrode assembly electrically connected to said current source and supported by said low current component;
    a second electrode assembly electrically connected to said current source and supported by said low current components; and
    a conductive fluid supported by said low current component for facilitating a flow of electric current across the tissue surface,
    wherein each of said first and second electrode assemblies comprises:
        a magnetic electrode, and
        a high current component made from a ferro-magnetic material, said high current component being electrically connected to said current source and being releasably magnetically coupled to said magnetic electrode, and,
    wherein said low current component comprises:
        a generally planar upper layer; and
        a generally planar lower layer disposed substantially parallel with said upper layer, said lower layer being adapted to contact the tissue surface and said conductive fluid being disposed between said upper layer and said lower layer, and
    wherein said magnetic electrode of each of said first and second electrode assemblies is supported on said lower layer and protrudes through said upper layer for said releasable magnetic coupling to said high current component.

2. An apparatus as defined in claim 1, wherein said magnetic electrode of each of said first and second electrode assemblies contacts said conductive fluid.

3. An apparatus as defined in claim 2, wherein said high current component of each of said first and second electrode assembly does not contact said lower layer of said low current component.

4. An apparatus as defined in claim 1, wherein at least one of said first and second electrode assemblies comprises:
    a high current component fixed in said low current component.

5. An apparatus as defined in claim 1, further comprising a current multiplexor electronically connected between said current source and said first and second electrode assemblies.

6. An apparatus as defined in claim 1, further comprising a third electrode assembly, said third electrode assembly comprising a high current component rigidly connected to a non-current component via a snap connection, the non-current component being embedded in the low current component.

7. An apparatus as defined in claim 6,
    wherein the non-current component protrudes through the upper layer of the low current component and makes contact with but does not protrude through the lower layer of the low current component.

8. An apparatus as defined in claim 1, wherein the first electrode assembly comprises a high current component rigidly connected to a magnetic electrode and the second electrode assembly comprises a high current component connected to a magnetic electrode via a proximity connection, the magnetic electrode being embedded inside an upper layer of the low current component.

9. An apparatus as defined in claim 6, wherein said non-current member is supported by and protrudes through said low current component for making contact with the tissue surface.

10. An apparatus as defined in claim 9, wherein said high current component of said third electrode assembly is suspended within the conductive fluid disposed between an upper and lower layer of said low current component.

11. An apparatus as defined in claim 1, further comprising:
    a headgear strap adapted to be secured to a patient's head, the low current component being supported by the headgear strap.

12. An apparatus as defined in claim 1, wherein the conductivity of the high current component of each electrode assembly is selected to be greater than 50 times the conductivity of the low current component, and wherein the minimum distance between the high current component and tissue surface is greater than 0.1 cm.

13. An apparatus as defined in claim 1, wherein the distance between the upper and lower surface of the low conductivity component is less than 5 cm but more than 0.5 cm, and wherein the minimum distance between any magnetic components is 1 cm, and wherein the high current components are positioned in a low current component such that top and bottom ends are exposed out of the low current component.

\* \* \* \* \*